United States Patent
Whitcomb et al.

(10) Patent No.: US 6,406,846 B1
(45) Date of Patent: Jun. 18, 2002

(54) METHOD FOR DETERMINING WHETHER A HUMAN PATIENT IS SUSCEPTIBLE TO HEREDITARY PANCREATITIS, AND PRIMERS THEREFORE

(75) Inventors: David Whitcomb, 9609 Parkedge Dr., Allison Park, PA (US) 15101; Garth D. Ehrlich; Michael C. Gorry, both of Pittsburgh, PA (US)

(73) Assignee: David Whitcomb, Allison Park, PA (US)

( * ) Notice: Subject to any disclaimer, the term of this patent is extended or adjusted under 35 U.S.C. 154(b) by 0 days.

(21) Appl. No.: 08/949,344

(22) Filed: Oct. 14, 1997

(51) Int. Cl.[7] ............................ C12Q 01/68; C07H 4/21
(52) U.S. Cl. ........................................ 435/6; 536/24.33
(58) Field of Search .................. 435/6, 91.2; 536/24.33

(56) References Cited

PUBLICATIONS

Férec et al. J. Med. Genet. (1999) 36:228–232.*
Dasouki et al. Am. J. Med. Genet. (1998) 77:47–53.*
Teich et al. Human Mutation 12:39–43 (1998).*
Whitcomb et al. GUT (1999) 45/3:317–322.*
Gorry et al. Gastroenterology (Oct. 1997) 113:1063–1068.*
Whitcomb et al. Nature Genetics (1996) 14:141–145.*
Witt et al. Gastroenterology (1999) 117:7–10.*

* cited by examiner

*Primary Examiner*—Lisa B. Arthur
(74) *Attorney, Agent, or Firm*—Angel M. Schwartz

(57) ABSTRACT

A method for determining whether a human patient is susceptible to hereditary pancreatitis. The method comprises the steps of obtaining nucleic acid from the human patient. Then there is the step of checking the nucleic acid for a mutation that indicates hereditary pancreatitis. A primer which reacts with a human trypsinogen gene to identify hereditary pancreatitis. A method for detecting in a human a mutation in a trypsinogen gene indicative of hereditary pancreatitis. The invention comprises the steps of obtaining a sample having DNA of the patient. Then there is the step of processing the sample so the DNA will be recognized by a desired restriction enzyme. Next there is the step of introducing the desired restriction enzyme to the DNA wherein the recognizing of the desired restriction enzyme to the DNA indicates the presence of the mutation.

10 Claims, 3 Drawing Sheets

METHOD FOR DETERMINING WHETHER A HUMAN PATIENT IS SUSCEPTIBLE TO HEREDITARY PANCREATITIS, AND PRIMERS THEREFORE

FIELD OF THE INVENTION

The present invention is related to determining whether a human patient is susceptible to hereditary pancreatitis. More specifically, the present invention is related to determining whether a human patient is susceptible to hereditary pancreatitis by identifying a single G to A transition mutation in the third exon of cationic trypsinogen, or digesting the trypsinogen gene in exon III with Afl III.

BACKGROUND OF THE INVENTION

Hereditary pancreatitis (HP) is an autosomal dominant disorder with 80% penetrance and variable expressivity [Perrault, J. Hereditary pancreatitis. *Gastroenterol. Clin. North Am.* 23:743–752 (1994); Madraso-de la Garza, J., Hill, I., Lebenthal, E. Hereditary pancreatitis. In: Go V, ed. *The Pancreas: Biology, Pathobiology, and Disease*. 2nd ed. New York: Raven, 1095–1101 (1993); Whitcomb, D. C., Preston, R. A., Aston, C. E., Sossenheimer, M. J., Barua, P. S., Zhang, Y., Wong-Chong, A., White, G., Wood, P., Gates, L. K., Jr., Ulrich, C., Martin, S. P., Post, J. C., and Ehrlich, G. D. A gene for hereditary pancreatitis maps to chromosome 7q35. *Gastroenterology* 110, 1975–1980 (1996); Bodic, L. L., Bignon, J. D., Raguenes, O., Mercier, B., Georgelin, T., Schnee, M., Soulard, F., Gagne, K., Bonneville, F., Muller, J. Y., Bachner, L., and Ferec, C. The hereditary pancreatitis gene maps to long arm of chromosome 7. *Hum. Molec. Genet.* 5, 549–554 (1996)]. Nearly 100 kindreds have been reported world-wide since the genetic nature of this disorder was recognized by Comfort and Steinberg in 1952 [Madraso-de la Garza, J., Hill, I., Lebenthal, E. Hereditary pancreatitis. In: Go V, ed. *The Pancreas: Biology, Pathobiology, and Disease*. 2nd ed. New York: Raven, 1095–1101 (1993); Comfort, M. and Steinberg, A. Pedigree of a family with hereditary chronic relapsing pancreatitis. *Gastroenterology* 21, 54 (1952)]. The majority of the families are of white European ancestry, but affected kindreds have been reported in Japan, India, and among other ethnic groups [Perrault, J. Hereditary pancreatitis. *Gastroenterol. Clin. North Am.* 23:743–752 (1994)]. HP is characterized by recurrent bouts of severe epigastric pain with onset, usually developing before ten years of age. The clinical, laboratory and pathologic features of HP are indistinguishable from attacks of pancreatitis from other causes. In addition to recurrent acute attacks, many HP patients progress to complicated chronic pancreatitis characterized by pancreatic calcifications, pseudocysts, chronic abdominal pain, pancreatic exocrine failure, diabetes mellitus and/or pancreatic cancer [Perrault, J. Hereditary pancreatitis. *Gastroenterol. Clin. North Am.* 23:743–752 (1994); Madraso-de la Garza, J., Hill, I., Lebenthal, E. Hereditary pancreatitis. In: Go V, ed. *The Pancreas: Biology, Pathobiology, and Disease*. 2nd ed. New York: Raven, 1095–1101 (1993)]. Despite years of research, no unique morphologic or biochemical markers have been identified for HP, and the pathophysiologic mechanisms that lead to intermittent attacks of acute pancreatitis remain obscure. Therefore, no rational or effective preventative strategies have been developed, and treatment consists solely of supportive care.

Because of the absence of biochemical markers specific for HP, attention has focused on identifying the HP disease gene. The availability of a high-density map of the human genome, based on polymorphic simple tandem repeat (STR) markers, and familial S0 linkage analysis made it possible to identify an HP gene locus within the q35 region of chromosome seven [Whitcomb, D. C., Preston, R. A., Aston, C. E., Sossenheimer, M. J., Barua, P. S., Zhang, Y., Wong-Chong, A., White, G., Wood, P., Gates, L. K., Jr., Ulrich, C., Martin, S. P., Post, J. C., and Ehrlich, G. D. A gene for hereditary pancreatitis maps to chromosome 7q35. *Gastroenterology* 110, 1975–1980 (1996); Bodic, L. L., Bignon, J. D., Raguenes, O., Mercier, B., Georgelin, T., Schnee, M., Soulard, F., Gagne, K., Bonneville, F., Muller, J. Y., Bachner, L., and Ferec, C. The hereditary pancreatitis gene maps to long arm of chromosome 7. *Hum. Molec. Genet.* 5, 549–554 (1996)]. It was thus desired to identify and sequence the HP gene to determine the site of the disease-causing mutation(s) in an effort to understand the molecular mechanism leading to HP. Several previously mapped genes on chromosome 7q were considered candidates for the HP disease gene because they are known to be expressed in the exocrine pancreas and encode enzymes that could potentially activate digestive enzymes within the pancreas. The hypothesis that pancreatitis results from inappropriate activation of pancreatic proenzymes was first promulgated 100 years ago and subsequently was demonstrated to be an experimental model for pancreatitis [Chiara, H. Ueber selbstverdauung des menschlichen pankreas. *Zeitschrift fur heilkunde* 17, 69–96 (1896); Steer, M. L., and Meldolesi, J. The cell biology of experimental pancreatitis. *N. Engl. J. Med.* 316 (3), 144–50, (1987)]. Although carboxypeptidase A1 (CPA1) was considered the primary candidate by Le Bodic [Bodic, L. L., Bignon, J. D., Raguenes, O., Mercier, B., Georgelin, T., Schnee, M., Soulard, F., Gagne, K., Bonneville, F., Muller, J. Y., Bachner, L., and Ferec, C. The hereditary pancreatitis gene maps to long arm of chromosome 7. *Hum. Molec. Genet.* 5, 549–554 (1996)], this gene mapped centromeric to the HP locus defined by obligate recombinations in an HP linkage study [Whitcomb, D. C., Preston, R. A., Aston, C. E., Sossenheimer, M. J., Barua, P. S., Zhang, Y., Wong-Chong, A., White, G., Wood, P., Gates, L. K., Jr., Ulrich, C., Martin, S. P., Post, J. C., and Ehrlich, G. D. A gene for hereditary pancreatitis maps to chromosome 7q35. *Gastroenterology* 110, 1975–1980 (1996); Stewart, E. A., Craik, C. S., Hake, L., and Bowcock, A. M. Human carboxypeptidase A identifies a BglII RFLP and maps to 7q31-qter. *Am. J. Hum. Genet.* 46 (4): 795–800, (1990); Rommens, J. M., Zengerling, S., Burns, J., Melmer, G., Kerem, B. S., Plavsic, N., Zsiga, M., Kennedy, D., Markiewicz, D., Rozmahel, R., et al. Identification and regional localization of DNA markers on chromosome 7 for the cloning of the cystic fibrosis gene. *Am. J. Hum. Genet.* 43 (5), 645–63 (1988); Rommens, J. M., Iannuzzi, M. C., Kerem, B., Drumm, M. L., Melmer, G., Dean, M., Rozmahel, R., Cole, J. L., Kennedy D., Hidaka, N., et al. Identification of the cystic fibrosis gene: chromosome walking and jumping. *Science*. 245 (4922): 1059–65 (1989); Martise, T. C., Perlin, M., and Chakravarti, A. Automated construction of genetic linkage maps using an expert system (MultiMap): a human genome linkage map. *Nature Genetics*. 6 (4), 384–90 (1994)] and was, therefore, excluded from further consideration. However, at least eight trypsinogen genes are located on chromosome 7q35 between the STR markers D7S495 and D7S498 and within the V and D-C segments of the complex T-cell receptor β chain gene locus (TCRβ) [Rowen, L., Koop, B. F., Hood, L. The Complete 685-Kilobase DNA Sequence of the Human_T Cell Receptor Locus. *Science* (1996)]. Trypsinogen is an inactive proenzyme for trypsin, which becomes active when an eight amino acid amino-terminal peptide is removed. Although small amounts of trypsin are normally generated within the pancreas, this active trypsin is usually rapidly inactivated before pancreatic autodigestion occurs. Thus, the trypsinogen genes were considered primary candidates for the HP disease gene.

The entire 685 kilobase (kb) TCRβ-trypsinogen locus has recently been sequenced by Rowen et al., as part of the largest human genome sequencing project completed to date [Rowen, L., Koop, B. F., Hood, L. The Complete 685-Kilobase DNA Sequence of the Human_T Cell Receptor Locus. *Science* (1996) ]. As a result of this study, eight trypsinogen-like genes were sequenced and identified that map within the TCR β locus. Three were located at the 5' end of the locus and were determined by sequence analysis to be pseudogenes. Another group of five trypsinogen genes, including the previously identified cationic and anionic pancreatic trypsinogen genes [Emi, M., Nakamura, Y., Owaga, M., et al. Cloning, characterization and nucleotide sequences of two cDNAs encoding human pancreatic trypsinogens. *Gene* 41, 305–310 (1986); Tani, T., Kawashima, I., Mita, K., Takiguchi, Y. Nucleotide sequence of the human pancreatic tryspinogen III cDNA. *Nucleic Acids Res* 18, 1631 (1990); Weingand, U., Corbach, S., Minn, A., Kang, J., Muller-Hill, B. Cloning of the cDNA encoding human brain trypsinogen and characterization of its product. *Gene* 136, 167–175 (1993)], were found to be in a cluster located between the $V_β 4S1$ and the $D_β 1$ elements near the 3' end of the TCRβ locus. Based on comparisons with the pancreatic cDNAs in Genbank, one of the newly identified trypsinogen-like genes (T6 or TRYC, in the nomenclature of Rowen et al., reference 12) may also be functional, as it does not contain any stop codons or frameshift mutations within the predicted exonic regions. However, no corresponding cDNAs have been identified to date. The two other trypsinogen-like genes located within this 70 kilobase cluster are not likely to be expressed due to nonsense mutations (e.g. stop codons) and/or frameshift mutations [Rowen, L., Koop, B. F., Hood, L. The Complete 685-Kilobase DNA Sequence of the Human_T Cell Receptor Locus. *Science* (1996)].

These five trypsinogen genes are highly homologous, each residing within a tandemly duplicated 10 kb segment and each being composed of five exons. The extremely high degree of DNA sequence homology (>91%) present among this cluster of five trypsinogen genes demanded that highly specific sequence analysis strategies be developed for mutational screening. This was necessary to ensure that each sequencing run contained only the two alleles corresponding to a single gene, thereby permitting detection of heterozygotes, and not a dozen or more alleles from multiple related trypsinogen-like genes which would make detection of heterozygotes nearly impossible. The initial DNA sequencing effort focused on the trypsinogen genes that were known to be expressed, specifically cationic trypsinogen and anionic trypsinogen [Emi, M., Nakamura, Y., Owaga, M., et al. Cloning, characterization and nucleotide sequences of two cDNAs encoding human pancreatic trypsinogens. *Gene* 41, 305–310 (1986); Tani, T., Kawashima, I., Mita, K., Takiguchi, Y. Nucleotide sequence of the human pancreatic tryspinogen III cDNA. *Nucleic Acids Res* 18, 1631 (1990)] using members of the S-family [McElroy, R., and Christiansen, P. A. Hereditary pancreatitis in a kinship association with portal vein thrombosis. *Am. J. Med.* 52, 228–241 (1972)]. This strategy was accomplished by sequencing each of the five exons from the specifically cationic trypsinogen and anionic trypsinogen genes individually using a gene-specific, nested PCR strategy. Generation of mixed sequence data, by the simultaneous amplification of more than one of the closely related trypsinogen genes, was avoided by basing each of the two nested PCR primer sets used for each exon-specific amplification on minor differences within the introns. This provided for the direct amplification and sequencing of each exon from both the cationic and anionic trypsinogen genes, in their entirety, from genomic DNA. Comparison of the DNA sequences generated from the PCR amplifications of control specimens with the published sequence from these regions revealed 100% concordance, thus confirming the utility of the nested primer approach for gene-specific mutational screening.

SUMMARY OF THE INVENTION

The present invention pertains to a method for determining whether a human patient is susceptible to hereditary pancreatitis. The method comprises the steps of obtaining nucleic acid from the human patient. Then there is the step of checking the nucleic acid for a mutation that indicates hereditary pancreatitis.

The present invention pertains to a set of PCR primers which reacts with a human trypsinogen gene to identify hereditary pancreatitis. The primer is preferably either U306 GGTCCTGGGTCTCATACCTT (5' outer) (SEQ ID NO 11), L1197 GGGTAGGAGGCTTCACACTT (3' outer) (SEQ ID NO 15), U329 TGACCCACATCCCTCTGCTG (5' inner/sequencing) (SEQ ID NO 12), or L924 TCTCCATTTGTC-CTGTCTCT (3' inner/sequencing) (SEQ ID NO 16) PCR amplification and cycle sequencing. Alternatively, the primers are TGTGAGGACATTCCTTGCGA (SEQ ID NO 5), TCTTCCTGAAAATTTTGACT (SEQ ID NO 18), ACAGAGACTTGGGAGCCACAGG (SEQ ID NO 6), GATACTTGCCTGCTTTTCTCA (SEQ ID NO 7), CGC-CACCCCTAACATGCTATTG (SEQ ID NO 9), CCATCT-TACCCAACCTCAGTAG (SEQ ID NO 10).

The present invention pertains to a method for detecting in a human a mutation in a trypsinogen gene indicative of hereditary pancreatitis. The invention comprises the steps of obtaining a sample having DNA of the patient. Then there is the 5 step of processing the sample so the trypsinogen genes within the DNA will be amplified by the specific primers. Next there is the step of introducing the desired restriction enzyme to the DNA wherein the digestion of the DNA by the desired restriction enzyme or direct DNA sequencing of the amplified gene indicates the presence of the mutation.

A G:A transition in the cationic trypsinogen gene is specifically associated with the HP phenotype. This mutation encodes an Arg:His substitution at residue 117, was observed in all HP affected individuals and obligate carriers from five kindreds; it was not observed in individuals who married into the families, nor was it observed in 140 unrelated individuals. X-ray crystal structure analysis, molecular modeling, and protein digest data suggest that the Arg 117 residue is a trypsin-sensitive site. Cleavage at this site is part of a fail-safe mechanism by which trypsin, that is activated within the pancreas, may be inactivated and that loss of this cleavage site would permit autodigestion resulting in pancreatitis.

BRIEF DESCRIPTION OF THE DRAWINGS

In the accompanying drawings, the preferred embodiment of the invention and preferred methods of practicing the invention are illustrated in which.

DESCRIPTION OF THE PREFERRED EMBODIMENT

Figure 1A:
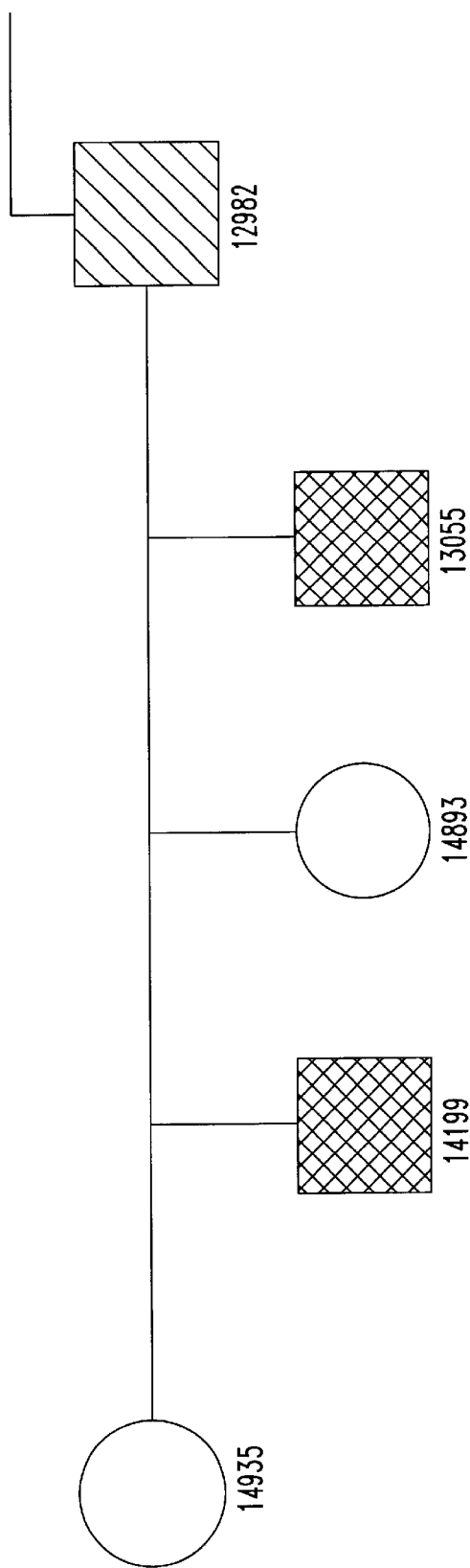
FIG. 1A shows partial pedigree of one of the HP kindreds.

The present invention pertains to a method for determining whether a human patient is susceptible to hereditary pancreatitis. The method comprises the steps of obtaining nucleic acid from the human patient. Then there is the step of checking the nucleic acid for a mutation that indicates hereditary pancreatitis.

Preferably, the checking step includes the step of identifying the presence of the mutation in the trypsinogen gene of the patient. The identifying step preferably includes the step of identifying the presence of the mutation in the cationic trypsinogen. The identifying step preferably includes the step of identifying the mutation in the third exon of the cationic trypsinogen. Preferably, the mutation is a single G to A transition mutation resulting in a substitution of histidine for arginine at amino acid #117 (R117H).

The identifying step includes the step of testing for the presence of the mutation using PCR amplification and cycle sequencing of the third exon of cationic trypsinogen. Preferably the testing step includes the step of using either U306 GGTCCTGGGTCTCATACCTT (5' outer) (SEQ ID NO 11), L1197 GGGTAGGAGGCTTCACACTT (3' outer) (SEQ ID NO 15), U329 TGACCCACATCCCTCTGCTG (5' inner/sequencing) (SEQ ID NO 12), or L924 TCTCCATTTGTC-CTGTCTCT (3' inner/sequencing) (SEQ ID NO 16) primers in the PCR amplification and cycle sequencing. Then there is the step of performing DNA sequencing on the amplification products.

Alternatively, the checking step includes the step of introducing Afl III with cationic trypsinogen exon III amplification products; and screening for division of trypsinogen gene or PCR amplification products.

The present invention pertains to a primer which reacts with a human trypsinogen gene to identify hereditary pancreatitis. The primer is preferably either U306 GGTC-CTGGGTCTCATACCTT (5' outer) (SEQ ID NO 11), L1197 GGGTAGGAGGCTTCACACTT (3' outer) (SEQ ID NO 15), U329 TGACCCACATCCCTCTGCTG (5' inner/sequencing) (SEQ ID NO 12), or L924 TCTCCATTTGTC-CTGTCTCT (3' inner/sequencing) (SEQ ID NO 16). Alternatively, the primer is either TGTGAGGACATTCCT-TGCGA (SEQ ID NO 5), TCTTCCTGAAAATTTTGACT (SEQ ID NO 8), ACAGAGACTTGGGAGCCACAGG (SEQ ID NO 6), GATACTTGCCTGCTTTTCTCA (SEQ ID NO 7), CGCCACCCCTAACATGCTATTG (SEQ ID NO 9), or CCATCTTACCCAACCTCAGTAG (SEQ ID NO 10).

The present invention pertains to a method for detecting in a human a mutation in a trypsinogen gene indicative of hereditary pancreatitis. The invention comprises the steps of obtaining a sample having DNA of the patient. Then there is the step of processing the sample so the DNA will bind to a desired restriction enzyme. Next there is the step of introducing the desired restriction enzyme to the DNA wherein the binding of the desired restriction enzyme to the DNA indicates the presence of the mutation.

Preferably, the processing step includes the step of processing the sample so the DNA will bind to the PCR primers desired restriction enzyme at a restriction enzyme recognition site. The processing of the sample is well known in the art. For instance if blood is drawn from a patient, the cells therein are nucleated to release the DNA, the DNA is purified, etc. by known techniques. The restriction enzyme is preferably Afl III. The site is preferably a G:A mutation in the third exon of cationic trypsinogen.

In the operation of the preferred embodiment, mutational screening analyses for each of the exons from the cationic and anionic trypsinogen genes were performed for multiple affected and unaffected HP family members. A single G to A transition mutation was identified in the third exon of cationic trypsinogen (FIG. 1) from all of the HP affected individuals and the obligate carriers examined from the S-family. This mutation results in an Arg(CGC) to His (CAC) substitution at amino acid residue 105 of trypsin (#117 in the more common chymotrypsin numbering system). Subsequently, a total of 42 family members including: 20 HP affected; 6 obligate carriers; and 16 unaffected family members from five different HP kindreds (four from the United States and one from Italy) were tested for the presence of this mutation using PCR amplification and cycle sequencing of the third exon of cationic trypsinogen.

A nested PCR strategy was employed wherein both the inner and outer sets of primers were designed such that the 31 base was positioned on a gene-specific polymorphism in an attempt to minimize amplification of related trypsinogen genes from within the cluster. Reaction conditions for all amplifications consisted of 50 mM KCl, 10 mM Tris*HCl (pH 8.3), 2.5 mM $MgCl_2$, 200_M of each of the 4 DNTPS (DATP, dCTP, dGTP, and dTTP). Cycling conditions for all PCR reactions consisted of an initial 3 minute denaturation step at 95° C., followed by 40 cycles at 94° C.×10"/64° C.×10"/72° C.×2', with a final 10' elongation step at 72° C.

The primers used to support the nested PCR for exon 3 of the human cationic trypsinogen gene were: U306 GGTC-CTGGGTCTCATACCTT (5' outer primer) (SEQ ID NO 11); L1197 GGGTAGGAGGCTTCACACTT (3' outer primer) (SEQ ID NO 15); U329 TGACCCACATCCCTCT-GCTG (5' inner/sequencing primer) (SEQ ID NO 12); L924 TCTCCATTTGTCCTGTCTCT (3' inner/sequencing primer) (SEQ ID NO 16). DNA sequencing reactions were performed using the Perkin Elmer (Foster City, Calif.) cycle sequencing kits and dye-terminator chemistry according to the manufacturers recommendations. All DNA sequencing was performed on an Applied Biosystems Inc (Foster City, Calif. 373A automated DNA sequencer equipped with a five color wheel. Sequence alignments were performed using DNA Sequencher™ (GeneCodes Corp; Ann Arbor Mich.).

All affected and obligate carriers examined from each of these five kindreds displayed the same G:A transition in codon 117, but none of the obligate unaffected members (individuals who married into the family) carried the mutation. Thus, the Arg:His mutation at residue 117 represents a consistent mutation in all cases of HP examined to date. The finding of identical mutations in five separate kindreds raised the possibility that these families might be distantly related and that the mutation is centuries old. Subsequent haplotyping studies revealed that all four of the American families displayed the same high risk haplotype over a 4 centiMorgan region encompassing 7 STR markers confirming the likelihood that these kindreds share a common ancestor, although no link could be found through eight generations. The fifth family, from Naples, Italy, displayed a unique haplotype indicating that the same mutation had occurred on at least two occasions. [Cucchiara, S., Staiano, A., Minella, R., Uomo, G., Cipolletta, L. Hereditary Pancreatitis: Report of the second kindred in Italy. *J. Ped. Gastro. Nutr.* 3, 422–425 (1990), incorporated by reference herein].

Figure 2:
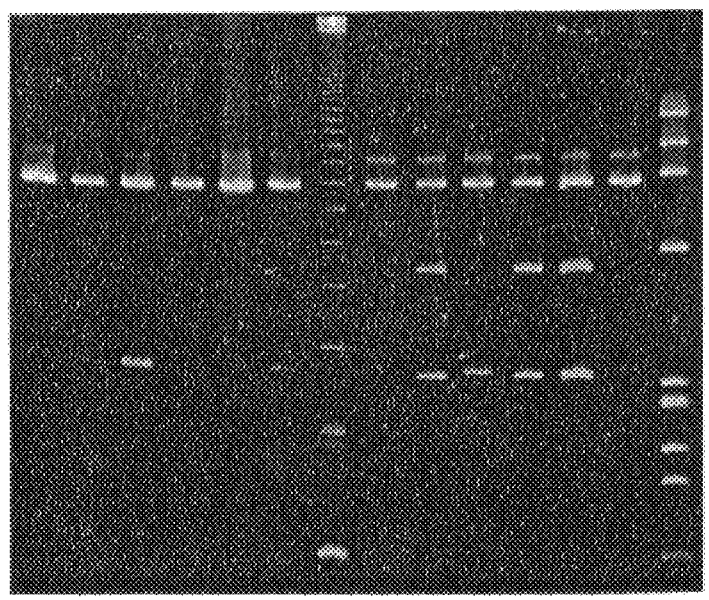
FIG. 2 shows ethidium bromide-stained agarose gel of PCR-amplified exon 3 products from the human cationic trypsinogen gene using the primers and the results of Afl III digestion demonstrating the presence of a G:A mutation in HP.

To rule out the minor possibility that the observed G:A mutation seen in the HP kindreds might be a present in the population-at-large as a natural polymorphism, a population-based study was performed. The G:A mutation, at Arg 117, creates a novel restriction enzyme recognition site for Afl III (New England Biolabs; Beverly, Mass.) which provided a facile means to screen for the presumptive HP mutation (FIG. 2). Using the cationic trypsinogen exon 3-specific nested primer pairs, 140 unrelated individuals chosen from our clinical database (no repeated surnames) were evaluated for the presence of the presumptive HP mutation. As with the obligate unaffected members of the HP kindreds, none of the 140 controls possessed the G:A mutation as assayed by the lack of Afl III digestion of the amplified exonic DNA. These data essentially rule out the possibility that the observed mutation is not HP-specific.

Figure 3:
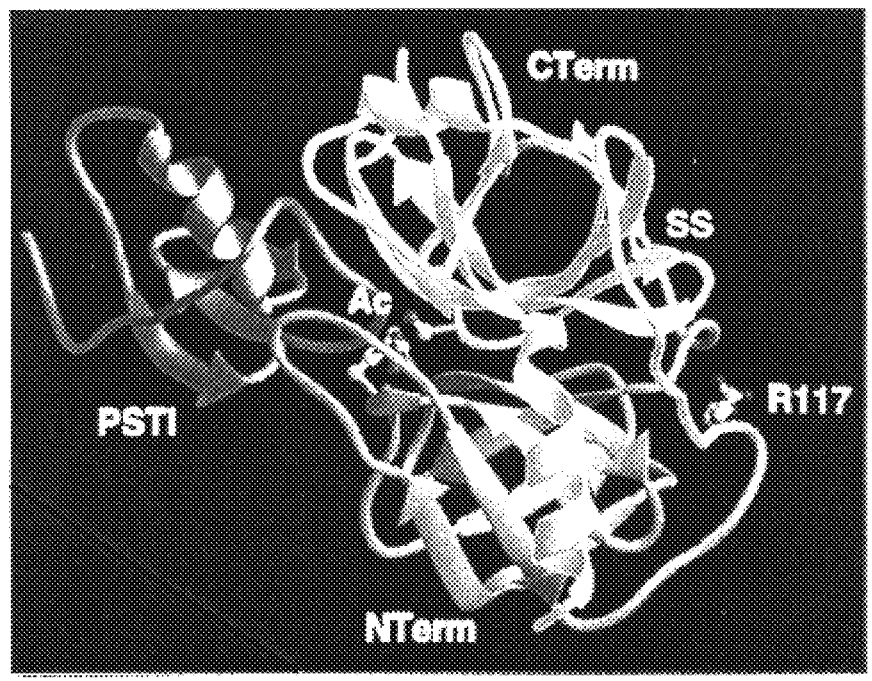
FIG. 3 shows a ribbon diagram for the trypsinogen-trypsinogen complex.

Examination of the X-ray crystal structure of cationic trypsinogen-trypsin inhibitor complex (Brookhaven Protein Data Bank, and Bernstein, F. C., Koetzle, T. F., Williams, G. F., Meyer, E. E., Jr., Brice, M. D., Rodgers, J. R., Kennard, O., Shimanouchi, T., Tasumi, M. The Protein Data Bank: a computer-based archival file for macromolecular structures. *J. Mol. Biol.* 112, 535–542 (1977); Bolognesi, M., Gatti, G., Menagatti, E., Guarneri, M., Marquart, M., Papamokos, E., Huber, R. Three-dimensional structure of the complex between pancreatic secretory trypsin inhibitor (Kazal type) and trypsinogen at 1.8 Å resolution. Structure solution, crystallographic refinement and preliminary structural interpretation. *J. Mol. Biol.* 162, 839–868 (1982)) reveals the three-dimensional position of Arg117 on the face of the trypsin molecule opposite that for the catalytic site and trypsin inhibitor binding site (FIG. 3). Analysis of this structure was performed on a silicon graphics IRIS indigo R 4000 using 1 TGS for the trypsinogen pancreatic secretion trypsin inhibitor complex. This suggested that an Arg 117 to His 117 mutation would have little effect on the tertiary structure of trypsin, alter the catalytic activity or interfere with trypsin inhibitor binding (S. Swaminathan unpublished results, 1996) However, it is also evident that Arg 117 is in a critical position in the peptide chain connecting the two globular domains of the trypsin molecule. Since trypsin-like serine proteases hydrolyze peptide chains at arginine and lysine residues, the Arg 117 of the wild-type protein should be susceptible to hydrolysis by these enzymes. Indeed, in vitro experiments have demonstrated that Arg 117 is the primary site for proteolysis of trypsin [Higaki, J. N., Light, A. The identification of neotrypsinogens in samples of bovine trypsinogen. *Anal. Biochem.* 148, 111–120 (1985); Rovery, M. Limited proteolyses in pancreatic chymotrypsinogens and trypsinogens. *Biochemie* 70, 1131–1135 (1988), incorporated by reference herein]. Cleavage between Arg 117 and Val 118 in vitro does not immediately inactivate trypsin, possibly because the two globular domains remain linked by a disulfide bond [Higaki, J. N., Light, A. The identification of neotrypsinogens in samples of bovine trypsinogen. *Anal. Biochem.* 148, 111–120 (1985); Rovery, M. Limited proteolyses in pancreatic chymotrypsinogens and trypsinogens. *Biochemie* 70, 1131–1135 (1988), incorporated by reference herein]. However, disruption of this disulfide bond after the Arg 117 cleavage does permanently inactivates trypsin [Higaki, J. N., Light, A. Independent refolding of domains in the pancreatic serine proteinases. *J. Biol. Chem.* 261, 10606–10609 (1986), incorporated by reference herein]. Furthermore, trypsin is rapidly inactivated in pancreatic juice suggesting that the Arg 117 hydrolysis may expose additional proteolytic sites, within what is termed the autolysis loop, to active zymogens [Bolognesi, M., Gatti, G., Menagatti, E., Guarneri, M., Marquart, M., Papamokos, E., Huber, R. Three-dimensional structure of the complex between pancreatic secretory trypsin inhibitor (Kazal type) and trypsinogen at 1.8 A resolution. Structure solution, crystallographic refinement and preliminary structural interpretation. *J. Mol. Biol.* 162, 839–868 (1982); Rinderknecht, H., Renner, I. G., Abramson, S. B., Carmack, C. Mesotrypsin: a new inhibitor-resistant protease from a zymogen in human pancreatic tissue and fluid. *Gastroenterology* 86, 681–692 (1984); Rinderknecht, H. Activation of Pancreatic Zymogens: Normal Activation, Premature Intrapancreatic Activation, Protective Mechanisms Against Inappropriate Activation. *Dig. Dis. Sci.* 31, 314–321 (1986); Rinderknecht, H., Adham, N. F., Renner, I. G., Carmack, C. A possible self-destruct mechanism preventing pancreatic autodigestion. *Int. J . Pancreatol* 3, 33–34 (1988) and (15), incorporated by reference herein]. The Arg 117 to His 117 mutation would render this site resistant to trypsin-like proteases preventing trypsin from being inactivated by this mechanism.

Figure 4B:
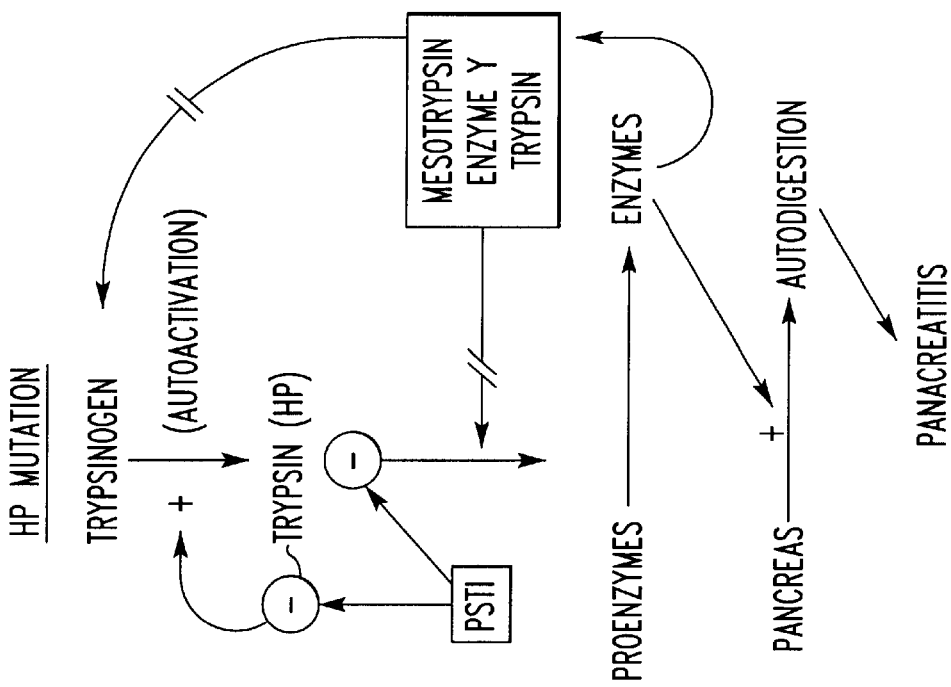
FIG. 4B shows the mechanism by which mutant (HP) trypsin activation, in amounts that exceed the inhibitory capacity of PSTI, is resistant to inactivation and that results in unchecked activation of proenzymes.
Figure 4A:
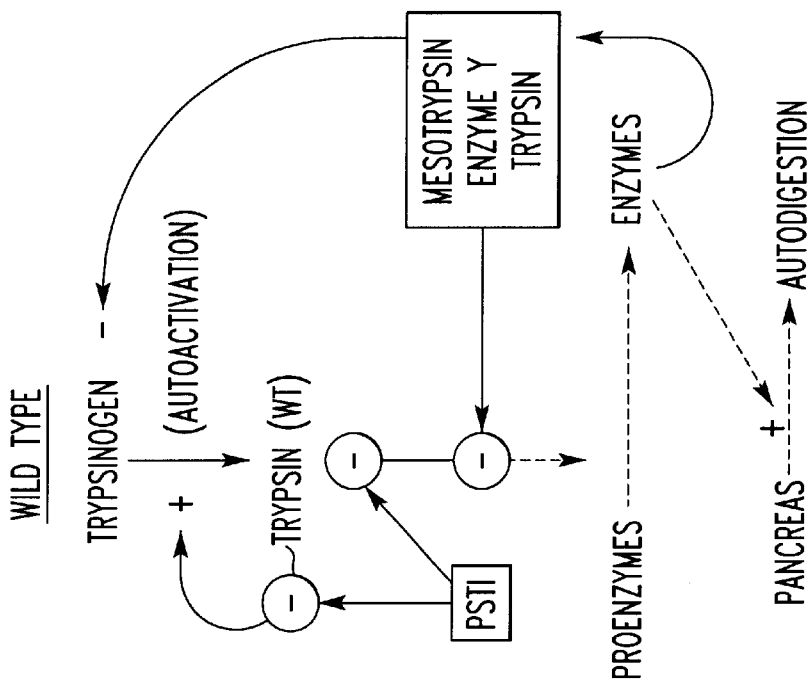
FIG. 4A shows the mechanism by which wild-type trypsin is inactivated during limited autoactivation of trypsinogen to active trypsin within pancreatic acinar cells.

Although trace amounts of trypsin can be identified within the normal pancreas, a more general activation of digestive enzymes within the pancreas leads to autodigestion and acute pancreatitis [Chiara, H. Ueber selbstverdauung des menschlichen parcreas. *Zeitschrift fur heilkunde* 17, 69–96 (1896); Steer, M. L., and Meldolesi, J. The cell biology of experimental pancreatitis. *N. Engl. J. Med.* 316 (3), 144–50, (1987), incorporated by reference herein]. The pancreas employs an array of mechanisms to prevent this problem [Rinderknecht, H. Pancreatic Secretory Enzymes. *The Pancreas: Biology, Pathobiology, and Disease* (ed. Go, V. L., DiMagno, E. P., Gardner, J. D, Lebenthal, E., Reber, H. A., Scheele, G. A.) 219–251 (Raven Press, New York, ed. 2, 1993), incorporated by reference herein]. All proteolytic enzymes, phospholipase A2 and colipase are synthesized as inactive proenzymes (zymogens). These proenzymes are sequestered from other subcellular components within membrane-bound zymogen granules. Activation of these digestive enzymes normally occurs outside the pancreas when intestinal enterokinase hydrolyzes trypsinogen to form active trypsin. Trypsin subsequently catalyzes its own conversion from trypsinogen to trypsin as well as converting all other proenzymes to their active form within the intestine. Since trace amounts of trypsin normally becomes activated within pancreatic acinar cells, two protective mechanisms are available to prevent the digestive enzyme activation cascade and pancreatic autodigestion (FIG. 4A). The first line of defense is pancreatic secretory trypsin inhibitor (PSTI), a 56 amino acid peptide that reversibly inhibits up to 20% of potentially available trypsin activity [Rinderknecht, H. Pancreatic Secretory Enzymes. *The Pancreas: Biology, Pathobiology, and Disease* (ed. Go, V. L., DiMagno, E. P., Gardner, J. D, Lebenthal, E., Reber, H. A., Scheele, G. A.) 219–251 (Raven Press, New York, ed. 2, 1993); Sweet, R. M., Wright, H. T., Janin, J., Chothia, C. H., Blow, D. M. Crystal structure of the complex of porcine trypsin with soybean trypsin inhibitor (Kunitz) at 2.6-A resolution. *Biochemistry* 13, 4212–4228 (1974); Laskowski, M. Jr., Ikunoshin, K. Protein inhibitors of proteinases. *Annu. Rev. Biochem.* 49, 593–626 (1980); Yamamoto, T., Nakamura, Y., Nishide, J., Emi, M., Ogawa, M., Mori, T., Matsubara, K. Molecular cloning and nucleotide sequence of human pancreatic secretory trypsin inhibitor (PSTI) CDNA. *Biochem. Biophys. Res. Commun.* 132, 605–612 (1985), incorporated by reference herein]. If trypsin activity overwhelms the inhibitory potential of PSTI then trypsin-like enzyme(s) [Rinderknecht, H. Pancreatic Secretory Enzymes. *The Pancreas: Biology, Pathobiology, and Disease* (ed. Go, V. L., DiMagno, E. P., Gardner, J. D, Lebenthal, E., Reber, H. A., Scheele, G. A.) 219–251 (Raven Press, New York, ed. 2, 1993), incorporated by reference herein] are activated that hydrolyze trypsin and other zymogens, thereby serving as a second or 'fail-safe' line of defense against initiating autodigestion and pancreatitis. Thus, excessive activation of trypsin would result in self-destruction of the zymogen granules' content. Based on this model, individuals with the HP disease gene allele would be protected from pancreatic autodigestion and pancreatitis as long as the level of trypsin activity was less than the inhibitory capacity of PSTI. Once trypsin activity exceeds the inhibitory potential of PSTI, then unopposed trypsin activity would ensue because the final self-destruct mechanism for inappropriately activated trypsin would be blocked by the absence of the Arg 117 cleavage site (FIG. 4B).

The process of inappropriate trypsin activation is especially important in humans. Cationic trypsinogen, which represents two-thirds of trypsin activity in normal human pancreatic juice, differs from the cationic trypsinogen of other species by its propensity to autoactivate, especially at a pH below 6 [Dassell, B., Kay, J. Zymogens of proteolytic enzymes. *Science* 180, 1022–1027 (1973); Bieger, W., Scheele, G. Two-dimensional isoelectric focusing/sodium dodecylsulfate gel electrophoresis of protein mixtures containing active or potentially active proteases. Analysis of human exocrine pancreatic proteins. *Anal. Biochem.* 109, 222–230 (1980); Figarella, C., Amouric, M., Guy-Crotee, O. Proteolysis of human trypsinogen. I. Pathogenetic implications in chronic pancreatitis. *Biochem. Biophys. Res. Commun.* 118, 154–161 (1984), incorporated by reference herein]. Since the rate of trypsinogen activation is greatly increased by trypsin, a trypsin-sensitive inactivation mechanism would appear to be critical. Rinderknect, et al [Higaki, J. N., Light, A. Independent refolding of domains in the pancreatic serine proteinases. *J. Biol. Chem.* 261, 10606–10609 (1986); Rinderknecht, H., Renner, I. G., Abramson, S. B., Carmack, C. Mesotrypsin: a new inhibitor-resistant protease from a zymogen in human pancreatic tissue and fluid. *Gastroenterology* 86, 681–692 (1984); Rinderknecht, H. Activation of Pancreatic Zymogens: Normal Activation, Premature Intrapancreatic Activation, Protective Mechanisms Against Inappropriate Activation. *Dig. Dis. Sci.* 31, 314–321 (1986); Rinderknecht, H., Adham, N. F., Renner, I. G., Carmack, C. A possible self-destruct mechanism preventing pancreatic autodigestion. *Int. J. Pancreatol* 3, 33–34 (1988) and [Weingand, U., Corbach, S., Minn, A., Kang, J., Muller-Hill, B. Cloning of the cDNA encoding human brain trypsinogen and characterization of its product. *Gene* 136, 167–175 (1993); Rinderknecht, H. Pancreatic Secretory Enzymes. *The Pancreas: Biology, Pathobiology, and Disease* (ed. Go, V. L., DiMagno, E. P., Gardner, J. D, Lebenthal, E., Reber, H. A., Scheele, G. A.) 219–251 (Raven Press, New York, ed. 2, 1993), incorporated by reference herein] have described at least two trypsin-like proteases, mesotrypsin and enzyme Y. that are found in the exocrine pancreas, are activated by trypsin, and in turn rapidly degrade trypsin and other zymogens to inert products in in vitro systems. Mesotrypsin represents a minor trypsin species (5%) that is completely resistant to PSTI neutralization. When activated by trypsin, mesotrypsin hydrolysis zymogens to inert products, even in the presence of PSTI. Enzyme Y appears to be a serine protease that differs from all other known pancreatic enzymes. When added to pancreatic juice with low PSTI content enzyme Y causes rapid inactivation of zymogens without significant activation of proenzymes or reduction of PSTI. In addition, trypsin itself will catalyze trypsin degradation [Higaki, J. N., Light, A. Independent refolding of domains in the pancreatic serine proteinases. *J. Biol. Chem.* 261, 10606–10609 (1986); Rinderknecht, H., Renner, I. G., Abramson, S. B., Carmack, C. Mesotrypsin: a new inhibitor-resistant protease from a zymogen in human pancreatic tissue and fluid. *Gastroenterology* 86, 681–692 (1984); Rinderknecht, H. Activation of Pancreatic Zymogens: Normal Activation, Premature Intrapancreatic Activation, Protective Mechanisms Against Inappropriate Activation. *Dig. Dis. Sci.* 31, 314–321 (1986), incorporated by reference herein]. Thus, at least three pancreatic enzymes have been identified that are activated by trypsin that serve as feed-back inhibitors by digesting trypsin at arginine or lysine residues. Mutation of trypsin at Arg 117 would render trypsin resistant to hydrolysis at this site by any of these three enzymes.

Since the HP mutation permits uncontrolled trypsin activity by the nature of its inability to be cleaved, once the enzyme is activated, the phenotype is present in heterozygotes. This is in agreement with the autosomal dominant pattern of inheritance observed for HP. Furthermore, this predicts that attacks of acute pancreatitis would occur only occasionally in patients carrying the HP allele such as when rates of intrapancreatic activation of trypsinogen overwhelm the protective effects of PSTI. Indeed, in HP patients, attacks of acute pancreatitis occur intermittently, often at times of unusual pancreatic stress such as after large meals or with excessive alcohol use [Perrault, J. Hereditary pancreatitis. *Gastroenterol. Clin. North Am.* 23:743–752 (1994); Madraso-de la Garza, J., Hill, I., Lebenthal, E. Hereditary pancreatitis. In: Go V, ed. *The Pancreas: Biology, Pathobiology, and Disease*. 2nd ed. New York: Raven, 1095–1101 (1993); Whitcomb, D. C., Preston, R. A., Aston, C. E., Sossenheimer, M. J., Parua, P. S., Zhang, Y., Wong-Chong, A., White, G., Wood, P., Gates, L. K., Jr., Ulrich, C., Martin, S. P., Post, J. C., and Ehrlich, G. D. A gene for hereditary pancreatitis maps to chromosome 7q35. *Gastroenterology* 110, 1975–1980 (1996), incorporated by reference herein].

These data suggest that HP results from a genetic defect that disrupts a critical component of a self-protective mechanism that permits non-affected individuals to digest their food without the risk of pancreatitis from autodigestion. HP represents an important and serious disease in which determination of the pathophysiologic mechanism will be central to the development of strategies for prevention and treatment. Now that the disease gene is known, individuals who carry the gene can be identified before pancreatitis begins. Furthermore, the mechanism for HP will aid in the design of strategies for preventing or controlling the development of the clinical manifestations of the disease. Finally, HP represents an excellent, relevant human model of acute and chronic pancreatitis that may provide insights into the pathophysiology of alcoholic, idiopathic and other types of pancreatitis in man.

Diagnostic criteria for the HP patients and unaffected relatives from the "S-family" [McElroy, R., and Christiansen, P. A. Hereditary pancreatitis in a kinship association with portal vein thrombosis. *Am. J. Med.* 52, 228–241 (1972), incorporated by reference herein] and the HP kindreds in New York, North Carolina, Florida and Naples, Italy were as previously described [Whitcomb, D. C., Preston, R. A., Aston, C. E., Sossenheimer, M. J., Barua, P. S., Zhang, Y., Wong-Chong, A., White, G., Wood, P., Gates, L. K., Jr., Ulrich, C., Martin, S. P., Post, J. C., and Ehrlich, G. D. A gene for hereditary pancreatitis maps to chromosome 7q35. *Gastroenterology* 110, 1975–1980 (1996); McElroy, R., and Christiansen, P. A. Hereditary pancreatitis in a kinship association with portal vein thrombosis. *Am. J. Med.* 52, 228–241 (1972), incorporated by reference herein]. Patient recruitment and interview were conducted by the Midwest Multicenter Pancreatic Study Group and members of the International Hereditary Pancreatitis Study Group (Lowenfels unpublished data).

Figure 1B:
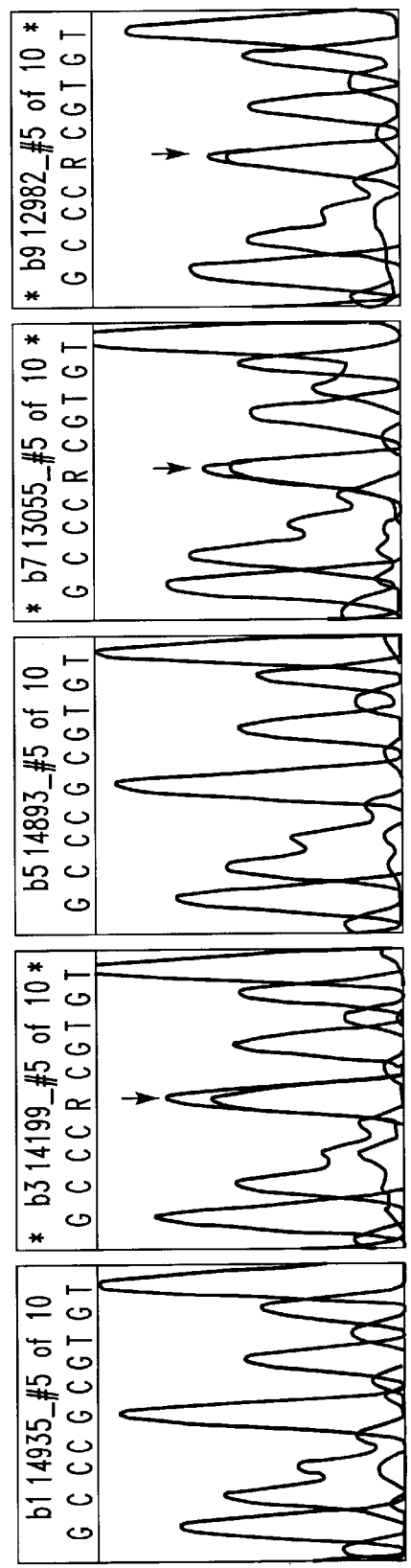
FIG. 1B shows DNA sequencing electropherograms, aligned with the pedigree in the top panel, showing the DNA sequence of the human cationic trypsinogen gene in the region of the HP mutation.

FIG. 1A shows partial pedigree of one of the HP kindreds. Circles represent females; squares represent males; solid boxes represent affected individuals; open boxes represent unaffected individuals; hashed boxes represent obligate carriers. The integers below the boxes are laboratory accession numbers which correspond with the electropherograms in the bottom panel. FIG. 1B shows DNA sequencing electropherograms, aligned with the pedigree in the top panel, showing the DNA sequence of the human cationic trypsinogen gene in the region of the HP mutation. Specimens from HP affected family members (14199 & 13055) and an obligate carrier family member (12982) demonstrate heterozygosity at the fifth nucleotide in the frame, see arrows in the 2nd, 4th, and 5th bottom panels. The sequencing signal is almost exactly 50% G and 50% A for each of these three specimens. In contrast, the signal observed for the two unaffected family members (14935 & 14893) is 100% G which is in keeping with the published sequence for cationic trypsinogen. All DNA amplifications and sequencing was performed as described [Martise, T. C., Perlin, M., and Chakravarti, A. Automated construction of genetic linkage maps using an expert system (MultiMap): a human genome linkage map. *Nature Genetics.* 6 (4), 384–90 (1994); Rowen, L., Koop, B. F., Hood, L. The Complete 685-Kilobase DNA Sequence of the Human_T Cell Receptor Locus. *Science* (in press) (1996), incorporated by reference herein].

FIG. 2 shows ethidium bromide-stained agarose gel of PCR-amplified exon 3 products from the human cationic trypsinogen gene using the two external primers [Rowen, L., Koop, B. F., Hood, L. The Complete 685-Kilobase DNA Sequence of the Human_T Cell Receptor Locus. *Science* (in press) (1996), incorporated by reference herein]. Lanes 1–5 are undigested exon 3 amplified DNAs (911 bp) from the same HP family members depicted in FIG. 1 (all specimens are in the same order). Lane 6 is amplified exon 3 DNA from an unrelated control specimen. Lanes 7 and 14 contains DNA molecular weight markers. Lanes 8–13 are the same amplified DNAs in lanes 1–6 following digestion with Afl III which recognizes a novel site created by the HP G:A mutation. Note the appearance of the two lower molecular weight bands (565 and 346 bp, respectively ) in lanes 9, 11, and 12 which correspond to the Afl III digestion products from the two HP affected individuals (14199 & 13055) and the obligate HP carrier individual (12982). Together these two bands account for the HP mutant allele, and the remaining high molecular weight band (911 bp) corresponds to the normal allele. There is a faint artifactual band that appears in some of the undigested and some of the digested samples that is generated during the PCR amplification process which can be seen migrating just above the smaller of the two Afl III digest products. This is not a cleavage product and demonstrates the necessity of using a nested approach for sequencing. All restriction enzyme digests were performed overnight according to the manufacturers (New England Biolabs; Beverly Mass.) instructions, incorporated by reference herein, following concentration of the amplified DNA using Microcon-50 microconcentrators (Amicon). The agarose gel composition was 1% SeaKem Agarose and 1% Nuseive Agarose (FMC Corp; Rockland, Me.).

FIG. 3 shows a ribbon diagram for the trypsinogen-trypsinogen complex. The N-terminal domain (N-Term, blue) and C-terminal domain (C-Term, yellow) of trypsinogen are shown relative to Arg 117 (R117, shown with the amino acid side chain). The side chains of the amino acids of the catalytic site (His 57, Asp 102, Ser 195) are seen on the opposite face of the trypsinogen molecule from Arg 117 and below trypsin inhibitor (PSTI, red). An Arg 117 to His 117 mutation would prevent trypsin-like hydrolysis of the chain connecting the two domains that are required for trypsin activity.

FIG. 4A shows the trypsin self-destruct mechanism to prevent pancreatic autodigestion. Autoactivation and enzymatic activation of trypsinogen generate trace amounts of active trypsin within pancreatic acinar cells. Active trypsin is inhibited by a limited supply of trypsin inhibitor (PSTI). If trypsin activity exceeds the inhibitory capacity of PSTI, then proenzymes, including mesotrypsin and enzyme Y are activated. The activation of these enzymes is postulated to be part of a feed-back mechanism for inactivating wild-type (wt) trypsinogen, trypsin and other zymogens.

FIG. 4B shows mutant (HP) trypsin activation, in amounts that exceed the inhibitory capacity of PSTI, that results in unchecked activation of proenzymes. Since the Arg 117 cleavage site for mesotrypsin, enzyme Y and trypsin is replaced by His in the HP mutant trypsin, trypsin continues to activate trypsinogen and other zymogens unabated, leading to autodigestion of the pancreas and pancreatitis.

In summary, trypsinogen exon III amplification is as follows:

1) Dilute DNA sample to concentration of 5 ng/µL
2) Prepare the following "master mix":

| | | | |
|---|---|---|---|
| dH$_2$O | 40.25 µL | x | µL |
| 10X Taq buffer | 5.00 | x | µL |
| dNTP (25 µM) ? | 2.50 | x | µL |
| Taq polymerase (5 U/µL) | 0.25 | x | µL |
| | 48.00 µL total | | |

3) Aliquot 48.00 µL to each of the reaction tubes
4) Add 1.00 µL of desired DNA @ 5 ng/µL (0.1 ng/µL final)
5) Add 0.5 µL each of Tryp1 Exon 3 U306 and L1197 (0.1 µM final)
6) Start Method #60:
   File 61: 95° C., 3 minutes
   File 62: 94° C., 15 seconds/61° C., 15 seconds/72° C., 30 seconds—40X
   File 29: 40° C., forever Additionally, Exon 2 of the cationic trypsinogen gene has an A to T mutation that reveals hereditary pancreatitis. Mutational screening identified a single A to T mutation resulting in an asparagine to isoleucine transition mutation at position 21 (N21I) in cationic trypsinogen. The mutation was absent in 94 unrelated individuals, representing 188 unique chromosomes. The identification of a second mutation in the cationic trypsinogen gene (HP2) indicates a dominant role of trypsin in premature protease activation-mediated forms of acute pancreatitis. The pathogenesis of hereditary pancreatitis also indicates that chronic pancreatitis may result from recurrent acute pancreatitis. In regard to this A to T mutation, DNA sequence analysis of the genese encoding the cationic and anionic trypsinogen was performed. Using flanking intronic primers for each of the five exons of each gene, the genomic DNA was amplified with a nested PCR format followed by direct sequencing on an ABI 373 Automated sequencer as described above.

To rule out the minor possibility that the observed G:A mutation might be present in the population-at-large as a natural polymorphism, a population-based study was performed. Examination of the N21I mutation in HP2 failed to reveal the creation of a new restriction enzyme recognition site for known restriction enzymes, thereby precluding the use of restriction digest in population screening. Therefore, the second exon of the cationic trypsinogen gene was sequenced in 94 unrelated individuals (188 chromosomes) identified from the CGS clinical database as described above. The primers that reveal the A to T mutation in PCR amplification and sequence cycling are preferably upper int #2 TGTGAGGACATTCCTTGCGA (SEQ ID NO 5), lower int #2 TCTTCCTGAAAATTTTGACT (SEQ ID NO 8), upper int #1 seq ACAGAGACTTGGGAGCCACAGG (SEQ ID NO 6), lower into #1 seq GATACTTGCCTGCTTTTCTCA (SEQ ID NO 7), up seq CGCCACCCCTAACATGCTATTG (SEQ ID NO 9), low seq CCATCTTACCCAACCTCAGTAG (SEQ ID NO 10).

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for determining whether a human patient is susceptible to hereditary pancreatitis comprising the steps of:
obtaining nucleic acid from the human patient; and
analyzing the nucleic acid to identify the presence of a single G to A transition mutation in codon 117 in a third exon of a cationic trypsinogen gene that indicates hereditary pancreatitis.

2. A method as described in claim 1 wherein the identifying step includes the step of testing for the presence of the mutation using PCR amplification and cycle sequencing of the third exon of cationic trypsinogen gene.

3. A method as described in claim 2 wherein the testing step includes the step of using either U306 GGTCCTGGGTCTCATACCTT (5' outer) (SEQ ID NO 11), L1197 GGGTAGGAGGCTTCACACTT, (5' inner/sequencing) (SEQ ID NO 15), or U329 TGACCCACATCCCTCTGCTG (5' inner/sequencing) (SEQ ID NO 12), or L924 TCTCCATTTGTCCTGTCTCT (3' inner/sequencing) (SEQ ID NO 16) primers in the PCR amplification and cycle sequencing.

4. A method as described in claim 1 wherein the analyzing step includes the step of introducing Afl III with the nucleic acid; and screening for division of cationic trypsinogen gene PCR products.

5. A primer which anneals with a human trypsinogen gene to identify hereditary pancreatitis which is either U306 GGTCCTGGGTCTCATACCTT (5' outer) (SEQ ID NO 11), L1197 GGGTAGGAGGCTTCACACTT, (5' inner/sequencing) (SEQ ID NO 15), or U329 TGACCCACATCCCTCTGCTG (5' inner/sequencing) (SEQ ID NO 12), or L924 TCTCCATTTGGTCCTGTCTCT (3' inner/sequencing) (SEQ ID NO 16).

6. A method for detecting in a human patient a mutation in the cationic trypsinogen gene indicative of hereditary pancreatitis comprising the steps of:
obtaining a sample having DNA of the patient;
processing the sample so the DNA will be recognized by a restriction enzyme Afl III at a restriction enzyme recognition site wherein the site is a sequence which is created when the specific sequence in codon 117 in a third exon of the cationic trypsinogen gene is mutated from G to an A; and
introducing the desired restriction enzyme to the DNA wherein the recognition of mutant DNA sequence by the desired restriction enzyme indicates the presence of the mutation.

7. A method for determining whether a human patient is susceptible to hereditary pancreatitis comprising the steps of:
obtaining nucleic acid from the human patient; and
analyzing the nucleic acid to identify the presence of a mutation is a single A to T transition mutation at codon 21 in a second exon of a cationic trypsinogen gene that indicates hereditary pancreatitis.

8. A method as described in claim 7 wherein the identifying step includes the step of testing for the presence of the mutation using PCR amplification and cycle sequencing of the PCR products encompassing the second exon of the cationic trypsinogen gene.

9. A method as described in claim 8 wherein the testing step includes the step of using either upper int #2 TGTGAGGACATTCCTTGCGA (SEQ ID NO 5), lower int #2 TCTTCCTGAAAATTTTGACT (SEQ ID NO 8), upper int #1 seq ACAGAGACTTGGGAGCCACAGG (SEQ ID NO 6), lower int #1 seq GATACTTGCCTGCTTTTCTCA (SEQ ID NO 7), up seq CGCCACCCCTAACATGCTATTG (SEQ ID NO 9), or low seq CCATCTTACCCAACCTCAGTAG (SEQ ID NO 10).

10. A primer which anneals with a human trypsinogen gene to identify hereditary pancreatitis which is either upper int #2 TGTGAGGACATTCCTTGCGA (SEQ ID NO 5), lower int #2 TCTTCCTGAAAATTTTGACT (SEQ ID NO 8), upper int #1 seq ACAGAGACTTGGGAGCCACAGG (SEQ ID NO 6), lower int #1 seq GATACTTGCCTGCTTTTCTCA (SEQ ID NO 7) up seq CGCCACCCCTAACATGCTATTG (SEQ ID NO 9), low seq CCATCTTACCCAACCTCAGTAG (SEQ ID NO 10).

* * * * *

```
                            SEQUENCE LISTING (1) GENERAL INFORMATION:

(iii) NUMBER OF SEQUENCES: 44

(2) INFORMATION FOR SEQ ID NO: 1:

(i) SEQUENCE CHARACTERISTICS:
         (A) LENGTH: 21 BASES
         (B) TYPE: NUCLEIC ACID
         (C) STRANDEDNESS: SINGLE STRANDED
         (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
         (A) ORGANISM: Homo sapiens
         (B) STRAIN: N/A
         (C) INDIVIDUAL ISOLATE: N/A
         (D) DEVELOPMENTAL STAGE: GERM-LINE
         (E) HAPLOTYPE: N/A
         (F) TISSUE TYPE: BLOOD
         (G) CELL TYPE: LEUKOCYTES
         (H) CELL LINE: N/A
         (I) ORGANELLE: NUCLEUS (vii) IMMEDIATE SOURCE:
         (A) LIBRARY: N/A
         (B) CLONE: N/A (viii) POSITION IN GENOME:
         (A) CHROMOSOME/SEGMENT: 7q35
         (B) MAP POSITION: 157 CM FROM THE TOP OF CHROMOSOME 7
         (C) UNITS: centimorgans (ix) FEATURE:
         (A) NAME/KEY: TRYPSINOGEN GENE 1 (TRY4), TRYPSINOGEN GENE 2
             (TRY8)
         (B) LOCATION: GENBANK LOCUS U66061
         (C) IDENTIFICATION METHOD: Comparison of DNA sequences and/or
             restriction enzyme digestion patterns of experimentally
``` determined from polymerase chain reaction of genomic DNA
                    from patients with hereditary pancreatitis with sequence
                    in GenBank locus U66061.
            (D) OTHER INFORMATION: Mutations in trypsinogen are associated
                    with a phenotype of recurrent acute pancreatitis, chronic
                    pancreatitis and an increased risk for pancreatic cancer.

(x) PUBLICATION INFORMATION:
        (A) AUTHORS: Whitcomb DC, Gorry MC, Preston RA, Furey W,
                Sossenheimer MJ, Ulrich CD, Martin SP, Gates Jr LK,
                Amann ST, Toskes, PP, LIDDLE R, MCGRAHT K,
                UOMO G, POST JC, EHRLICH GD
        (B) TITLE: Hereditary pancreatitis is caused by a mutation
                in the cationic trypsinogen gene
        (C) JOURNAL: Nature Genetics
        (D) VOLUME: 14
        (E) ISSUE: 2
        (F) PAGES: 141-5
        (G) DATE: 15-10-96
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W,
                Gates Jr LK, Preston RA, Aston CE, Zhang Y, Ulrich C,
                Ehrlich GD, Whitcomb DC
        (B) TITLE: Multiple Mutations in the Cationic Trypsinogen
                Gene are Associated with Hereditary Pancreatitis
        (C) JOURNAL: Gastroenterology
        (D) VOLUME: 113
        (E) ISSUE: 4
        (F) PAGES: 1063-1068
        (G) DATE: 15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence
                of the human beta T cell receptor locus
        (C) JOURNAL: Science
        (D) VOLUME: 272
        (E) ISSUE: 5269
        (F) PAGES: 1755-1762
        (G) DATE: 6 21 96
        (H) DOCUMENT NUMBER: MEDLINE 96256474
        (I) FILING DATE:
        (J) PUBLICATION DATE: June 21, 1996
        (K) RELEVANT RESIDUES IN SEQ ID NO: From 130700 to 134500,
                172600 to 176300 (in GenBank sequence)

(xi) SEQUENCE DESCRIPTION: SEQ ID NO: 1:

CCC AAT AGG TGG AAA GAT TTG                                             21

(2) INFORMATION FOR SEQ ID NO: 2:

(i) SEQUENCE CHARACTERISTICS:
        (A) LENGTH: 22 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD

```
            (G) CELL TYPE: LEUKOCYTES
            (H) CELL LINE: N/A
            (I) ORGANELLE: NUCLEUS (vii) IMMEDIATE SOURCE:
            (A) LIBRARY: N/A
            (B) CLONE: N/A (viii) POSITION IN GENOME:
            (A) CHROMOSOME/SEGMENT: 7q35
            (B) MAP POSITION: 157 CM FROM THE TOP OF CHROMOSOME 7
            (C) UNITS: centimorgans (ix) FEATURE:
            (A) NAME/KEY: TRYPSINOGEN GENE 1 (TRY4), TRYPSINOGEN
                GENE 2 (TRY8)
            (B) LOCATION: GENBANK LOCUS U66061
            (C) IDENTIFICATION METHOD: Comparison of DNA sequences
                and/or restriction enzyme digestion patterns
                experimentally determined from polymerase chain
                reaction of genomic DNA from patients with hereditary
                pancreatitis with sequence in GenBank locus U66061.
            (D) OTHER INFORMATION: Mutations in trypsinogen are
                associated with a phenotype of recurrent acute
                pancreatitis, chronic pancreatitis and an increased
                risk for pancreatic cancer.

(x) PUBLICATION INFORMATION:
            (A) AUTHORS: Whitcomb DC, Gorry MC, Preston RA, Furey W,
                Sossenheimer MJ, Ulrich CD, Martin SP, Gates Jr LK,
                Amann ST, Toskes, PP, LIDDLE R, MCGRAHT K,
                UOMO G, POST JC, EHRLICH GD
            (B) TITLE: Hereditary pancreatitis is caused by a mutation
                in the cationic trypsinogen gene
            (C) JOURNAL: Nature Genetics
            (D) VOLUME: 14
            (E) ISSUE: 2
            (F) PAGES: 141-5
            (G) DATE:  15-10-96
            (H) DOCUMENT NUMBER: NA
            (I) FILING DATE:
            (J) PUBLICATION DATE: 15-10-96
            (K) RELEVANT RESIDUES IN SEQ ID NO: NA
            (A) AUTHORS: Gorry MC, Gabbaizedeh D, Furey W, Gates Jr LK,
                Preston RA, Aston CE, Zhang Y, Ulrich C, Ehrlich GD,
                Whitcomb DC
            (B) TITLE: Multiple Mutations in the Cationic Trypsinogen
                Gene are Associated with Hereditary Pancreatitis
            (C) JOURNAL: Gastroenterology
            (D) VOLUME: 113
            (E) ISSUE: 4
            (F) PAGES: 1063-1068
            (G) DATE:  15-10-96
            (H) DOCUMENT NUMBER: NA
            (I) FILING DATE:
            (J) PUBLICATION DATE: OCTOBER 1997
            (K) RELEVANT RESIDUES IN SEQ ID NO: NA
            (A) AUTHORS:Rowen,L, Koop BF, Hood L.
            (B) TITLE: The complete 685-kilobase DNA sequence of the
                human beta T cell receptor locus
            (C) JOURNAL: Science
            (D) VOLUME: 272
            (E) ISSUE: 5269
            (F) PAGES: 1755-1762
            (G) DATE: 6 21 96
            (H) DOCUMENT NUMBER: MEDLINE 96256474
            (I) FILING DATE:
            (J) PUBLICATION DATE: June 21, 1996
            (K) RELEVANT RESIDUES IN SEQ ID NO: From 130700 to 134500
                (in GenBank sequence)

(xi) SEQUENCE DESCRIPTION: SEQ ID NO: 2:

CCT CAC AGT CAC CTC CTC TCT G                                         22

(2) INFORMATION FOR SEQ ID NO: 3:

(i) SEQUENCE CHARACTERISTICS:
```

```
         (A) LENGTH: 20 BASES
         (B) TYPE: NUCLEIC ACID
         (C) STRANDEDNESS: SINGLE STRANDED
         (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
         (A) ORGANISM: Homo sapiens
         (B) STRAIN: N/A
         (C) INDIVIDUAL ISOLATE: N/A
         (D) DEVELOPMENTAL STAGE: GERM-LINE
         (E) HAPLOTYPE: N/A
         (F) TISSUE TYPE: BLOOD
         (G) CELL TYPE: LEUKOCYTES
         (H) CELL LINE: N/A
         (I) ORGANELLE: NUCLEUS (vii) IMMEDIATE SOURCE:
         (A) LIBRARY: N/A
         (B) CLONE: N/A (viii) POSITION IN GENOME:
         (A) CHROMOSOME/SEGMENT: 7q35
         (B) MAP POSITION: 157 CM FROM THE TOP OF CHROMOSOME 7
         (C) UNITS: centimorgans (ix) FEATURE:
         (A) NAME/KEY: TRYPSINOGEN GENE 1 (TRY4), TRYPSINOGEN GENE
             2 (TRY8)
         (B) LOCATION: GENBANK LOCUS U66061
         (C) IDENTIFICATION METHOD: Comparison of DNA sequences and/or
             restriction enzyme digestion patterns of experimentally
             determined from polymerase chain reaction of genomic DNA
             from patients with hereditary pancreatitis with
             sequence in GenBank locus U66061.
         (D) OTHER INFORMATION: Mutations in trypsinogen are associated
             with a phenotype of recurrent acute pancreatitis, chronic
             pancreatitis and an increased risk for pancreatic cancer.

(x) PUBLICATION INFORMATION:
         (A) AUTHORS: Whitcomb DC, Gorry MC, Preston RA, Furey W,
             Sossenheimer MJ, Ulrich CD, Martin SP, Gates Jr LK,
             Amann ST, Toskes, PP, LIDDLE R, MCGRAHT K, UOMO G,
             POST JC, EHRLICH GD
         (B) TITLE: Hereditary pancreatitis is caused by a mutation
             in the cationic trypsinogen gene
         (C) JOURNAL: Nature Genetics
         (D) VOLUME: 14
         (E) ISSUE: 2
         (F) PAGES: 141-5
         (G) DATE:  15-10-96
         (H) DOCUMENT NUMBER: NA
         (I) FILING DATE:
         (J) PUBLICATION DATE: 15-10-96
         (K) RELEVANT RESIDUES IN SEQ ID NO: NA
         (A) AUTHORS: Gorry MC, Gabbaizedeh D, Furey W, Gates Jr LK,
             Preston RA, Aston CE, Zhang Y, Ulrich C, Ehrlich GD,
             Whitcomb DC
         (B) TITLE: Multiple Mutations in the Cationic Trypsinogen
             Gene are Associated with Hereditary Pancreatitis
         (C) JOURNAL: Gastroenterology
         (D) VOLUME: 113
         (E) ISSUE: 4
         (F) PAGES: 1063-1068
         (G) DATE:  15-10-96
         (H) DOCUMENT NUMBER: NA
         (I) FILING DATE:
         (J) PUBLICATION DATE: OCTOBER 1997
         (K) RELEVANT RESIDUES IN SEQ ID NO: NA
         (A) AUTHORS:Rowen,L, Koop BF, Hood L.
         (B) TITLE: The complete 685-kilobase DNA sequence of the
             human beta T cell receptor locus
```

```
        (C) JOURNAL: Science
        (D) VOLUME: 272
        (E) ISSUE: 5269
        (F) PAGES: 1755-1762
        (G) DATE: 6 21 96
        (H) DOCUMENT NUMBER: MEDLINE 96256474
        (I) FILING DATE:
        (J) PUBLICATION DATE: June 21, 1996
        (K) RELEVANT RESIDUES IN SEQ ID NO: From 130700 to 134500
            (in GenBank sequence)

(xi) SEQUENCE DESCRIPTION: SEQ ID NO: 3:

TGA AGT CAA GGA GAA GGT GA                                              20

(2) INFORMATION FOR SEQ ID NO: 4:

(i) SEQUENCE CHARACTERISTICS:
        (A) LENGTH: 20 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN
            GENE 2 (TRY8)
        (B) LOCATION: GENBANK LOCUS U66061
        (C) IDENTIFICATION METHOD: Comparison of DNA sequences
            and/or restriction enzyme digestion patterns of
            experimentally determined from polymerase chain
            reaction of genomic DNA from patients with hereditary
            pancreatitis with sequence in GenBank locus U66061.
        (D) OTHER INFORMATION: Mutations in trypsinogen are
            associated with a phenotype of recurrent acute
            pancreatitis, chronic pancreatitis and an
            increased risk for pancreatic cancer.

(x) PUBLICATION INFORMATION:
        (A) AUTHORS: Whitcomb DC, Gorry MC, Preston RA,
            Furey W, Sossenheimer MJ, Ulrich CD, Martin SP,
            Gates Jr LK, Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE:  15-10-96
        (H) DOCUMENT NUMBER: NA
```

```
            (I) FILING DATE:
            (J) PUBLICATION DATE: 15-10-96
            (K) RELEVANT RESIDUES IN SEQ ID NO: NA
            (A) AUTHORS: Gorry MC, Gabbaizedeh D, Furey W, Gates Jr LK,
                Preston RA, Aston CE, Zhang Y, Ulrich C, Ehrlich GD,
                Whitcomb DC
            (B) TITLE: Multiple Mutations in the Cationic Trypsinogen
                Gene are Associated with Hereditary Pancreatitis
            (C) JOURNAL: Gastroenterology
            (D) VOLUME: 113
            (E) ISSUE: 4
            (F) PAGES: 1063-1068
            (G) DATE: 15-10-96
            (H) DOCUMENT NUMBER: NA
            (I) FILING DATE:
            (J) PUBLICATION DATE: OCTOBER 1997
            (K) RELEVANT RESIDUES IN SEQ ID NO: NA
            (A) AUTHORS:Rowen,L, Koop BF, Hood L.
            (B) TITLE: The complete 685-kilobase DNA sequence of the
                human beta T cell receptor locus
            (C) JOURNAL: Science
            (D) VOLUME: 272
            (E) ISSUE: 5269
            (F) PAGES: 1755-1762
            (G) DATE: 6 21 96
            (H) DOCUMENT NUMBER: MEDLINE 96256474
            (I) FILING DATE:
            (J) PUBLICATION DATE: June 21, 1996
            (K) RELEVANT RESIDUES IN SEQ ID NO: From 130700 to 134500
                (in GenBank sequence)

(xi) SEQUENCE DESCRIPTION: SEQ ID NO: 4:

TAT GCC AGA TGG AGG AAA CG                                          20

(2) INFORMATION FOR SEQ ID NO: 5:

(i) SEQUENCE CHARACTERISTICS:
        (A) LENGTH: 20 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
```

```
              from patients with hereditary pancreatitis with
              sequence in GenBank locus U66061.
       (D) OTHER INFORMATION: Mutations in trypsinogen are associated
              with a phenotype of recurrent acute pancreatitis, chronic
              pancreatitis and an increased risk for pancreatic cancer.

(x) PUBLICATION INFORMATION:
       (A) AUTHORS: Whitcomb DC, Gorry MC, Preston RA, Furey W,
              Sossenheimer MJ, Ulrich CD, Martin SP, Gates Jr LK,
              Amann ST, Toskes, PP, LIDDLE R, MCGRAHT K,
              UOMO G, POST JC, EHRLICH GD
       (B) TITLE: Hereditary pancreatitis is caused by a mutation
              in the cationic trypsinogen gene
       (C) JOURNAL: Nature Genetics
       (D) VOLUME: 14
       (E) ISSUE: 2
       (F) PAGES: 141-5
       (G) DATE:  15-10-96
       (H) DOCUMENT NUMBER: NA
       (I) FILING DATE:
       (J) PUBLICATION DATE: 15-10-96
       (K) RELEVANT RESIDUES IN SEQ ID NO: NA
       (A) AUTHORS: Gorry MC, Gabbaizedeh D, Furey W, Gates Jr LK,
              Preston RA, Aston CE, Zhang Y, Ulrich C, Ehrlich GD,
              Whitcomb DC
       (B) TITLE: Multiple Mutations in the Cationic Trypsinogen
              Gene are Associated with Hereditary Pancreatitis
       (C) JOURNAL: Gastroenterology
       (D) VOLUME: 113
       (E) ISSUE: 4
       (F) PAGES: 1063-1068
       (G) DATE:   15-10-96
       (H) DOCUMENT NUMBER: NA
       (I) FILING DATE:
       (J) PUBLICATION DATE: OCTOBER 1997
       (K) RELEVANT RESIDUES IN SEQ ID NO: NA
       (A) AUTHORS:Rowen,L, Koop BF, Hood L.
       (B) TITLE: The complete 685-kilobase DNA sequence of the
              human beta T cell receptor locus
       (C) JOURNAL: Science
       (D) VOLUME: 272
       (E) ISSUE: 5269
       (F) PAGES: 1755-1762
       (G) DATE: 6 21 96
       (H) DOCUMENT NUMBER: MEDLINE 96256474
       (I) FILING DATE:
       (J) PUBLICATION DATE: June 21, 1996
       (K) RELEVANT RESIDUES IN SEQ ID NO: From 130700 to 134500
              (in GenBank sequence)

(xi) SEQUENCE DESCRIPTION: SEQ ID NO: 5:

TGT GAG GAC ATT CCT TGC GA                                      20

(2) INFORMATION FOR SEQ ID NO: 6:

(i) SEQUENCE CHARACTERISTICS:
       (A) LENGTH: 22 BASES
       (B) TYPE: NUCLEIC ACID
       (C) STRANDEDNESS: SINGLE STRANDED
       (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
       (A) ORGANISM: Homo sapiens
       (B) STRAIN: N/A
       (C) INDIVIDUAL ISOLATE: N/A
       (D) DEVELOPMENTAL STAGE: GERM-LINE
       (E) HAPLOTYPE: N/A
       (F) TISSUE TYPE: BLOOD
       (G) CELL TYPE: LEUKOCYTES
```

(H) CELL LINE: N/A
            (I) ORGANELLE: NUCLEUS (vii) IMMEDIATE SOURCE:
            (A) LIBRARY: N/A
            (B) CLONE: N/A (viii) POSITION IN GENOME:
            (A) CHROMOSOME/SEGMENT: 7q35
            (B) MAP POSITION: 157 CM FROM THE TOP OF CHROMOSOME 7
            (C) UNITS: centimorgans (ix) FEATURE:
            (A) NAME/KEY: TRYPSINOGEN GENE 1 (TRY4), TRYPSINOGEN GENE
                2 (TRY8)
            (B) LOCATION: GENBANK LOCUS U66061
            (C) IDENTIFICATION METHOD: Comparison of DNA sequences and/or
                restriction enzyme digestion patterns of experimentally
                determined from polymerase chain reaction of genomic DNA
                from patients with hereditary pancreatitis with
                sequence in GenBank locus U66061.
            (D) OTHER INFORMATION: Mutations in trypsinogen are associated
                with a phenotype of recurrent acute pancreatitis,
                chronic pancreatitis and an increased risk for pancreatic
                cancer.

(x) PUBLICATION INFORMATION:
            (A) AUTHORS: Whitcomb DC, Gorry MC, Preston RA, Furey W,
                Sossenheimer MJ, Ulrich CD, Martin SP, Gates Jr LK,
                Amann ST, Toskes, PP, LIDDLE R, MCGRAHT K,
                UOMO G, POST JC, EHRLICH GD
            (B) TITLE: Hereditary pancreatitis is caused by a mutation
                in the cationic trypsinogen gene
            (C) JOURNAL: Nature Genetics
            (D) VOLUME: 14
            (E) ISSUE: 2
            (F) PAGES: 141-5
            (G) DATE: 15-10-96
            (H) DOCUMENT NUMBER: NA
            (I) FILING DATE:
            (J) PUBLICATION DATE: 15-10-96
            (K) RELEVANT RESIDUES IN SEQ ID NO: NA
            (A) AUTHORS: Gorry MC, Gabbaizedeh D, Furey W, Gates Jr LK,
                Preston RA, Aston CE, Zhang Y, Ulrich C, Ehrlich GD,
                Whitcomb DC
            (B) TITLE: Multiple Mutations in the Cationic Trypsinogen
                Gene are Associated with Hereditary Pancreatitis
            (C) JOURNAL: Gastroenterology
            (D) VOLUME: 113
            (E) ISSUE: 4
            (F) PAGES: 1063-1068
            (G) DATE: 15-10-96
            (H) DOCUMENT NUMBER: NA
            (I) FILING DATE:
            (J) PUBLICATION DATE: OCTOBER 1997
            (K) RELEVANT RESIDUES IN SEQ ID NO: NA
            (A) AUTHORS:Rowen,L, Koop BF, Hood L.
            (B) TITLE: The complete 685-kilobase DNA sequence of the
                human beta T cell receptor locus
            (C) JOURNAL: Science
            (D) VOLUME: 272
            (E) ISSUE: 5269
            (F) PAGES: 1755-1762
            (G) DATE: 6 21 96
            (H) DOCUMENT NUMBER: MEDLINE 96256474
            (I) FILING DATE:
            (J) PUBLICATION DATE: June 21, 1996
            (K) RELEVANT RESIDUES IN SEQ ID NO: From 130700 to 134500
                (in GenBank sequence)

(xi) SEQUENCE DESCRIPTION: SEQ ID NO: 6:

ACA GAG ACT TGG GAG CCA CAG G                                              22

(2) INFORMATION FOR SEQ ID NO: 7:

(i) SEQUENCE CHARACTERISTICS:
            (A) LENGTH: 21 BASES

```
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences
            and/or restriction enzyme digestion patterns of
            experimentally determined from polymerase chain
            reaction of genomic DNA from patients with hereditary
            pancreatitis with sequence in GenBank locus U66061.
        (D) OTHER INFORMATION: Mutations in trypsinogen are
            associated with a phenotype of recurrent acute
            pancreatitis, chronic pancreatitis and an
            increased risk for pancreatic cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE:  15-10-96
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
        (G) DATE:  15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the
            human beta T cell receptor locus
```

```
            (C) JOURNAL: Science
            (D) VOLUME: 272
            (E) ISSUE: 5269
            (F) PAGES: 1755-1762
            (G) DATE: 6 21 96
            (H) DOCUMENT NUMBER: MEDLINE 96256474
            (I) FILING DATE:
            (J) PUBLICATION DATE: June 21, 1996
            (K) RELEVANT RESIDUES IN SEQ ID NO: From 130700 to 134500
                (in GenBank sequence)

(xi) SEQUENCE DESCRIPTION: SEQ ID NO: 7:

GAT ACT TGC CTG CTT TTC TCA                                        21

(2) INFORMATION FOR SEQ ID NO: 8:

(i) SEQUENCE CHARACTERISTICS:
        (A) LENGTH: 20 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences
            and/or restriction enzyme digestion patterns of
            experimentally determined from polymerase chain
            reaction of genomic DNA from patients with hereditary
            pancreatitis with sequence in GenBank locus U66061.
        (D) OTHER INFORMATION: Mutations in trypsinogen are
            associated with a phenotype of recurrent acute
            pancreatitis, chronic pancreatitis and an
            increased risk for pancreatic cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE: 15-10-96
        (H) DOCUMENT NUMBER: NA
```

```
          (I) FILING DATE:
          (J) PUBLICATION DATE: 15-10-96
          (K) RELEVANT RESIDUES IN SEQ ID NO: NA
          (A) AUTHORS: Gorry MC, Gabbaizedeh D, Furey W, Gates Jr LK,
                Preston RA, Aston CE, Zhang Y, Ulrich C, Ehrlich GD,
                Whitcomb DC
          (B) TITLE: Multiple Mutations in the Cationic Trypsinogen
                Gene are Associated with Hereditary Pancreatitis
          (C) JOURNAL: Gastroenterology
          (D) VOLUME: 113
          (E) ISSUE: 4
          (F) PAGES: 1063-1068
          (G) DATE: 15-10-96
          (H) DOCUMENT NUMBER: NA
          (I) FILING DATE:
          (J) PUBLICATION DATE: OCTOBER 1997
          (K) RELEVANT RESIDUES IN SEQ ID NO: NA
          (A) AUTHORS:Rowen,L, Koop BF, Hood L.
          (B) TITLE: The complete 685-kilobase DNA sequence of the
                human beta T cell receptor locus
          (C) JOURNAL: Science
          (D) VOLUME: 272
          (E) ISSUE: 5269
          (F) PAGES: 1755-1762
          (G) DATE: 6 21 96
          (H) DOCUMENT NUMBER: MEDLINE 96256474
          (I) FILING DATE:
          (J) PUBLICATION DATE: June 21, 1996
          (K) RELEVANT RESIDUES IN SEQ ID NO: From 130700 to 134500
                (in GenBank sequence)

(xi) SEQUENCE DESCRIPTION: SEQ ID NO: 8:

TCT TCC TGA AAA TTT TGA CT                                           20

(2) INFORMATION FOR SEQ ID NO: 9:

(i) SEQUENCE CHARACTERISTICS:
          (A) LENGTH: 22 BASES
          (B) TYPE: NUCLEIC ACID
          (C) STRANDEDNESS: SINGLE STRANDED
          (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
          (A) ORGANISM: Homo sapiens
          (B) STRAIN: N/A
          (C) INDIVIDUAL ISOLATE: N/A
          (D) DEVELOPMENTAL STAGE: GERM-LINE
          (E) HAPLOTYPE: N/A
          (F) TISSUE TYPE: BLOOD
          (G) CELL TYPE: LEUKOCYTES
          (H) CELL LINE: N/A
          (I) ORGANELLE: NUCLEUS (vii) IMMEDIATE SOURCE:
          (A) LIBRARY: N/A
          (B) CLONE: N/A (viii) POSITION IN GENOME:
          (A) CHROMOSOME/SEGMENT: 7q35
          (B) MAP POSITION: 157 CM FROM THE TOP OF CHROMOSOME 7
          (C) UNITS: centimorgans (ix) FEATURE:
          (A) NAME/KEY: TRYPSINOGEN GENE 1 (TRY4), TRYPSINOGEN GENE 2
                (TRY8)
          (B) LOCATION: GENBANK LOCUS U66061
          (C) IDENTIFICATION METHOD: Comparison of DNA sequences and/or
                restriction enzyme digestion patterns of experimentally
                determined from polymerase chain reaction of genomic DNA
```

```
                from patients with hereditary pancreatitis with
                sequence in GenBank locus U66061.
        (D) OTHER INFORMATION: Mutations in trypsinogen are associated
            with a phenotype of recurrent acute pancreatitis,
            chronic pancreatitis and an increased risk for pancreatic
            cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE:  15-10-96
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
        (G) DATE:  15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the
            human beta T cell receptor locus
        (C) JOURNAL: Science
        (D) VOLUME: 272
        (E) ISSUE: 5269
        (F) PAGES: 1755-1762
        (G) DATE: 6 21 96
        (H) DOCUMENT NUMBER: MEDLINE 96256474
        (I) FILING DATE:
        (J) PUBLICATION DATE: June 21, 1996
        (K) RELEVANT RESIDUES IN SEQ ID NO: From 130700 to 134500,
            172600 to 176300 (in GenBank sequence)

(xi) SEQUENCE DESCRIPTION: SEQ ID NO: 9:

CGC CAC CCC TAA CAT GCT ATT G                                          22

(2) INFORMATION FOR SEQ ID NO: 10:

(i) SEQUENCE CHARACTERISTICS:
        (A) LENGTH: 22 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
```

```
            (G) CELL TYPE: LEUKOCYTES
            (H) CELL LINE: N/A
            (I) ORGANELLE: NUCLEUS (vii) IMMEDIATE SOURCE:
            (A) LIBRARY: N/A
            (B) CLONE: N/A (viii) POSITION IN GENOME:
            (A) CHROMOSOME/SEGMENT: 7q35
            (B) MAP POSITION: 157 CM FROM THE TOP OF CHROMOSOME 7
            (C) UNITS: centimorgans (ix) FEATURE:
            (A) NAME/KEY: TRYPSINOGEN GENE 1 (TRY4), TRYPSINOGEN GENE 2
                (TRY8)
            (B) LOCATION: GENBANK LOCUS U66061
            (C) IDENTIFICATION METHOD: Comparison of DNA sequences and/or
                restriction enzyme digestion patterns of experimentally
                determined from polymerase chain reaction of genomic DNA
                from patients with hereditary pancreatitis with
                sequence in GenBank locus U66061.
            (D) OTHER INFORMATION: Mutations in trypsinogen are associated
                with a phenotype of recurrent acute pancreatitis, chronic
                pancreatitis and an increased risk for pancreatic cancer.

(x) PUBLICATION INFORMATION:
            (A) AUTHORS: Whitcomb DC, Gorry MC, Preston RA, Furey W,
                Sossenheimer MJ, Ulrich CD, Martin SP, Gates Jr LK,
                Amann ST, Toskes, PP, LIDDLE R, MCGRAHT K,
                UOMO G, POST JC, EHRLICH GD
            (B) TITLE: Hereditary pancreatitis is caused by a mutation
                in the cationic trypsinogen gene
            (C) JOURNAL: Nature Genetics
            (D) VOLUME: 14
            (E) ISSUE: 2
            (F) PAGES: 141-5
            (G) DATE:  15-10-96
            (H) DOCUMENT NUMBER: NA
            (I) FILING DATE:
            (J) PUBLICATION DATE: 15-10-96
            (K) RELEVANT RESIDUES IN SEQ ID NO: NA
            (A) AUTHORS: Gorry MC, Gabbaizedeh D, Furey W, Gates Jr LK,
                Preston RA, Aston CE, Zhang Y, Ulrich C, Ehrlich GD,
                Whitcomb DC
            (B) TITLE: Multiple Mutations in the Cationic Trypsinogen
                Gene are Associated with Hereditary Pancreatitis
            (C) JOURNAL: Gastroenterology
            (D) VOLUME: 113
            (E) ISSUE: 4
            (F) PAGES: 1063-1068
            (G) DATE:  15-10-96
            (H) DOCUMENT NUMBER: NA
            (I) FILING DATE:
            (J) PUBLICATION DATE: OCTOBER 1997
            (K) RELEVANT RESIDUES IN SEQ ID NO: NA
            (A) AUTHORS:Rowen,L, Koop BF, Hood L.
            (B) TITLE: The complete 685-kilobase DNA sequence of the
                human beta T cell receptor locus
            (C) JOURNAL: Science
            (D) VOLUME: 272
            (E) ISSUE: 5269
            (F) PAGES: 1755-1762
            (G) DATE: 6 21 96
            (H) DOCUMENT NUMBER: MEDLINE 96256474
            (I) FILING DATE:
            (J) PUBLICATION DATE: June 21, 1996
            (K) RELEVANT RESIDUES IN SEQ ID NO: From 130700 to 134500
                (in GenBank sequence)

(xi) SEQUENCE DESCRIPTION: SEQ ID NO: 10:

CCA TCT TAC CCA ACC TCA GTA G                                           22

(2) INFORMATION FOR SEQ ID NO: 11:

(i) SEQUENCE CHARACTERISTICS:
          (A) LENGTH: 20 BASES
```

```
      (B) TYPE: NUCLEIC ACID
      (C) STRANDEDNESS: SINGLE STRANDED
      (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
      (A) ORGANISM: Homo sapiens
      (B) STRAIN: N/A
      (C) INDIVIDUAL ISOLATE: N/A
      (D) DEVELOPMENTAL STAGE: GERM-LINE
      (E) HAPLOTYPE: N/A
      (F) TISSUE TYPE: BLOOD
      (G) CELL TYPE: LEUKOCYTES
      (H) CELL LINE: N/A
      (I) ORGANELLE: NUCLEUS (vii) IMMEDIATE SOURCE:
      (A) LIBRARY: N/A
      (B) CLONE: N/A (viii) POSITION IN GENOME:
      (A) CHROMOSOME/SEGMENT: 7q35
      (B) MAP POSITION: 157 CM FROM THE TOP OF CHROMOSOME 7
      (C) UNITS: centimorgans (ix) FEATURE:
      (A) NAME/KEY: TRYPSINOGEN GENE 1 (TRY4), TRYPSINOGEN GENE 2
          (TRY8)
      (B) LOCATION: GENBANK LOCUS U66061
      (C) IDENTIFICATION METHOD: Comparison of DNA sequences and/or
          restriction enzyme digestion patterns of experimentally
          determined from polymerase chain reaction of genomic DNA
          from patients with hereditary pancreatitis with
          sequence in GenBank locus U66061.
      (D) OTHER INFORMATION: Mutations in trypsinogen are associated
          with a phenotype of recurrent acute pancreatitis, chronic
          pancreatitis and an increased risk for pancreatic cancer.

(x) PUBLICATION INFORMATION:
      (A) AUTHORS: Whitcomb DC, Gorry MC, Preston RA, Furey W,
          Sossenheimer MJ, Ulrich CD, Martin SP, Gates Jr LK,
          Amann ST, Toskes, PP, LIDDLE R, MCGRAHT K,
          UOMO G, POST JC, EHRLICH GD
      (B) TITLE: Hereditary pancreatitis is caused by a mutation
          in the cationic trypsinogen gene
      (C) JOURNAL: Nature Genetics
      (D) VOLUME: 14
      (E) ISSUE: 2
      (F) PAGES: 141-5
      (G) DATE:  15-10-96
      (H) DOCUMENT NUMBER: NA
      (I) FILING DATE:
      (J) PUBLICATION DATE: 15-10-96
      (K) RELEVANT RESIDUES IN SEQ ID NO: NA
      (A) AUTHORS: Gorry MC, Gabbaizedeh D, Furey W, Gates Jr LK,
          Preston RA, Aston CE, Zhang Y, Ulrich C, Ehrlich GD,
          Whitcomb DC
      (B) TITLE: Multiple Mutations in the Cationic Trypsinogen
          Gene are Associated with Hereditary Pancreatitis
      (C) JOURNAL: Gastroenterology
      (D) VOLUME: 113
      (E) ISSUE: 4
      (F) PAGES: 1063-1068
      (G) DATE:  15-10-96
      (H) DOCUMENT NUMBER: NA
      (I) FILING DATE:
      (J) PUBLICATION DATE: OCTOBER 1997
      (K) RELEVANT RESIDUES IN SEQ ID NO: NA
      (A) AUTHORS:Rowen,L, Koop BF, Hood L.
      (B) TITLE: The complete 685-kilobase DNA sequence of the
          human beta T cell receptor locus
      (C) JOURNAL: Science
```

```
            (D) VOLUME: 272
            (E) ISSUE: 5269
            (F) PAGES: 1755-1762
            (G) DATE: 6 21 96
            (H) DOCUMENT NUMBER: MEDLINE 96256474
            (I) FILING DATE:
            (J) PUBLICATION DATE: June 21, 1996
            (K) RELEVANT RESIDUES IN SEQ ID NO: From 130700 to 134500
                (in GenBank sequence)

(xi) SEQUENCE DESCRIPTION: SEQ ID NO: 11:

GGT CCT GGG TCT CAT ACC TT                                                    20

(2) INFORMATION FOR SEQ ID NO: 12:

(i) SEQUENCE CHARACTERISTICS:
            (A) LENGTH: 20 BASES
            (B) TYPE: NUCLEIC ACID
            (C) STRANDEDNESS: SINGLE STRANDED
            (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
            (A) ORGANISM: Homo sapiens
            (B) STRAIN: N/A
            (C) INDIVIDUAL ISOLATE: N/A
            (D) DEVELOPMENTAL STAGE: GERM-LINE
            (E) HAPLOTYPE: N/A
            (F) TISSUE TYPE: BLOOD
            (G) CELL TYPE: LEUKOCYTES
            (H) CELL LINE: N/A
            (I) ORGANELLE: NUCLEUS (vii) IMMEDIATE SOURCE:
            (A) LIBRARY: N/A
            (B) CLONE: N/A (viii) POSITION IN GENOME:
            (A) CHROMOSOME/SEGMENT: 7q35
            (B) MAP POSITION: 157 CM FROM THE TOP OF CHROMOSOME 7
            (C) UNITS: centimorgans (ix) FEATURE:
            (A) NAME/KEY: TRYPSINOGEN GENE 1 (TRY4), TRYPSINOGEN GENE 2
                (TRY8)
            (B) LOCATION: GENBANK LOCUS U66061
            (C) IDENTIFICATION METHOD: Comparison of DNA sequences and/or
                restriction enzyme digestion patterns of experimentally
                determined from polymerase chain reaction of genomic DNA
                from patients with hereditary pancreatitis with
                sequence in GenBank locus U66061.
            (D) OTHER INFORMATION: Mutations in trypsinogen are associated
                with a phenotype of recurrent acute pancreatitis, chronic
                pancreatitis and an increased risk for pancreatic cancer.

(x) PUBLICATION INFORMATION:
            (A) AUTHORS: Whitcomb DC, Gorry MC, Preston RA, Furey W,
                Sossenheimer MJ, Ulrich CD, Martin SP, Gates Jr LK,
                Amann ST, Toskes, PP, LIDDLE R, MCGRAHT K,
                UOMO G, POST JC, EHRLICH GD
            (B) TITLE: Hereditary pancreatitis is caused by a mutation
                in the cationic trypsinogen gene
            (C) JOURNAL: Nature Genetics
            (D) VOLUME: 14
            (E) ISSUE: 2
            (F) PAGES: 141-5
            (G) DATE:  15-10-96
            (H) DOCUMENT NUMBER: NA
            (I) FILING DATE:
            (J) PUBLICATION DATE: 15-10-96
```

```
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
        (G) DATE:  15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the human
            beta T cell receptor locus
        (C) JOURNAL: Science
        (D) VOLUME: 272
        (E) ISSUE: 5269
        (F) PAGES: 1755-1762
        (G) DATE: 6 21 96
        (H) DOCUMENT NUMBER: MEDLINE 96256474
        (I) FILING DATE:
        (J) PUBLICATION DATE: June 21, 1996
        (K) RELEVANT RESIDUES IN SEQ ID NO: From 130700 to 134500
            (in GenBank sequence)

(xi) SEQUENCE DESCRIPTION: SEQ ID NO: 12:

TGA CCC ACA TCC CTC TGC TG                                           20

(2) INFORMATION FOR SEQ ID NO: 13:

(i) SEQUENCE CHARACTERISTICS:
        (A) LENGTH: 24 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
            from patients with hereditary pancreatitis with
            sequence in GenBank locus U66061.
```

```
            (D) OTHER INFORMATION: Mutations in trypsinogen are associated
                with a phenotype of recurrent acute pancreatitis, chronic
                pancreatitis and an increased risk for pancreatic cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE:  15-10-96
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
        (G) DATE:  15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the
            human beta T cell receptor locus
        (C) JOURNAL: Science
        (D) VOLUME: 272
        (E) ISSUE: 5269
        (F) PAGES: 1755-1762
        (G) DATE: 6 21 96
        (H) DOCUMENT NUMBER: MEDLINE 96256474
        (I) FILING DATE:
        (J) PUBLICATION DATE: June 21, 1996
        (K) RELEVANT RESIDUES IN SEQ ID NO: From 130700 to 134500
            (in GenBank sequence)

(xi) SEQUENCE DESCRIPTION: SEQ ID NO: 13:

CAA GTT AAG GGG CAT GGT TTG TTC                                            24

(2) INFORMATION FOR SEQ ID NO: 14:

(i) SEQUENCE CHARACTERISTICS:
        (A) LENGTH: 24 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS
```

(vii) IMMEDIATE SOURCE:
              (A) LIBRARY: N/A
              (B) CLONE: N/A (viii) POSITION IN GENOME:
              (A) CHROMOSOME/SEGMENT: 7q35
              (B) MAP POSITION: 157 CM FROM THE TOP OF CHROMOSOME 7
              (C) UNITS: centimorgans (ix) FEATURE:
              (A) NAME/KEY: TRYPSINOGEN GENE 1 (TRY4), TRYPSINOGEN GENE 2
                  (TRY8)
              (B) LOCATION: GENBANK LOCUS U66061
              (C) IDENTIFICATION METHOD: Comparison of DNA sequences and/or
                  restriction enzyme digestion patterns of experimentally
                  determined from polymerase chain reaction of genomic DNA
                  from patients with hereditary pancreatitis with
                  sequence in GenBank locus U66061.
              (D) OTHER INFORMATION: Mutations in trypsinogen are associated
                  with a phenotype of recurrent acute pancreatitis, chronic
                  pancreatitis and an increased risk for pancreatic cancer.

(x) PUBLICATION INFORMATION:
              (A) AUTHORS: Whitcomb DC, Gorry MC, Preston RA, Furey W,
                  Sossenheimer MJ, Ulrich CD, Martin SP, Gates Jr LK,
                  Amann ST, Toskes, PP, LIDDLE R, MCGRAHT K,
                  UOMO G, POST JC, EHRLICH GD
              (B) TITLE: Hereditary pancreatitis is caused by a mutation
                  in the cationic trypsinogen gene
              (C) JOURNAL: Nature Genetics
              (D) VOLUME: 14
              (E) ISSUE: 2
              (F) PAGES: 141-5
              (G) DATE:  15-10-96
              (H) DOCUMENT NUMBER: NA
              (I) FILING DATE:
              (J) PUBLICATION DATE: 15-10-96
              (K) RELEVANT RESIDUES IN SEQ ID NO: NA
              (A) AUTHORS: Gorry MC, Gabbaizedeh D, Furey W, Gates Jr LK,
                  Preston RA, Aston CE, Zhang Y, Ulrich C, Ehrlich GD,
                  Whitcomb DC
              (B) TITLE: Multiple Mutations in the Cationic Trypsinogen
                  Gene are Associated with Hereditary Pancreatitis
              (C) JOURNAL: Gastroenterology
              (D) VOLUME: 113
              (E) ISSUE: 4
              (F) PAGES: 1063-1068
              (G) DATE:  15-10-96
              (H) DOCUMENT NUMBER: NA
              (I) FILING DATE:
              (J) PUBLICATION DATE: OCTOBER 1997
              (K) RELEVANT RESIDUES IN SEQ ID NO: NA
              (A) AUTHORS:Rowen,L, Koop BF, Hood L.
              (B) TITLE: The complete 685-kilobase DNA sequence of the
                  human beta T cell receptor locus
              (C) JOURNAL: Science
              (D) VOLUME: 272
              (E) ISSUE: 5269
              (F) PAGES: 1755-1762
              (G) DATE: 6 21 96
              (H) DOCUMENT NUMBER: MEDLINE 96256474
              (I) FILING DATE:
              (J) PUBLICATION DATE: June 21, 1996
              (K) RELEVANT RESIDUES IN SEQ ID NO: From 130700 to 134500
                  (in GenBank sequence)

(xi) SEQUENCE DESCRIPTION: SEQ ID NO: 14:

CTG GCT GTG GGA GAA GGT CTT CAC                                            24

(2) INFORMATION FOR SEQ ID NO: 15:

(i) SEQUENCE CHARACTERISTICS:
          (A) LENGTH: 20 BASES
          (B) TYPE: NUCLEIC ACID
          (C) STRANDEDNESS: SINGLE STRANDED
          (D) TOPOLOGY: LINEAR

```
      (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
           (A) ORGANISM: Homo sapiens
           (B) STRAIN: N/A
           (C) INDIVIDUAL ISOLATE: N/A
           (D) DEVELOPMENTAL STAGE: GERM-LINE
           (E) HAPLOTYPE: N/A
           (F) TISSUE TYPE: BLOOD
           (G) CELL TYPE: LEUKOCYTES
           (H) CELL LINE: N/A
           (I) ORGANELLE: NUCLEUS (vii) IMMEDIATE SOURCE:
           (A) LIBRARY: N/A
           (B) CLONE: N/A (viii) POSITION IN GENOME:
           (A) CHROMOSOME/SEGMENT: 7q35
           (B) MAP POSITION: 157 CM FROM THE TOP OF CHROMOSOME 7
           (C) UNITS: centimorgans (ix) FEATURE:
           (A) NAME/KEY: TRYPSINOGEN GENE 1 (TRY4), TRYPSINOGEN GENE 2
               (TRY8)
           (B) LOCATION: GENBANK LOCUS U66061
           (C) IDENTIFICATION METHOD: Comparison of DNA sequences and/or
               restriction enzyme digestion patterns of experimentally
               determined from polymerase chain reaction of genomic DNA
               from patients with hereditary pancreatitis with
               sequence in GenBank locus U66061.
           (D) OTHER INFORMATION: Mutations in trypsinogen are associated
               with a phenotype of recurrent acute pancreatitis, chronic
               pancreatitis and an increased risk for pancreatic cancer.

(x) PUBLICATION INFORMATION:
           (A) AUTHORS: Whitcomb DC, Gorry MC, Preston RA, Furey W,
               Sossenheimer MJ, Ulrich CD, Martin SP, Gates Jr LK,
               Amann ST, Toskes, PP, LIDDLE R, MCGRAHT K,
               UOMO G, POST JC, EHRLICH GD
           (B) TITLE: Hereditary pancreatitis is caused by a mutation
               in the cationic trypsinogen gene
           (C) JOURNAL: Nature Genetics
           (D) VOLUME: 14
           (E) ISSUE: 2
           (F) PAGES: 141-5
           (G) DATE:  15-10-96
           (H) DOCUMENT NUMBER: NA
           (I) FILING DATE:
           (J) PUBLICATION DATE: 15-10-96
           (K) RELEVANT RESIDUES IN SEQ ID NO: NA
           (A) AUTHORS: Gorry MC, Gabbaizedeh D, Furey W, Gates Jr LK,
               Preston RA, Aston CE, Zhang Y, Ulrich C, Ehrlich GD,
               Whitcomb DC
           (B) TITLE: Multiple Mutations in the Cationic Trypsinogen
               Gene are Associated with Hereditary Pancreatitis
           (C) JOURNAL: Gastroenterology
           (D) VOLUME: 113
           (E) ISSUE: 4
           (F) PAGES: 1063-1068
           (G) DATE:  15-10-96
           (H) DOCUMENT NUMBER: NA
           (I) FILING DATE:
           (J) PUBLICATION DATE: OCTOBER 1997
           (K) RELEVANT RESIDUES IN SEQ ID NO: NA
           (A) AUTHORS:Rowen,L, Koop BF, Hood L.
           (B) TITLE: The complete 685-kilobase DNA sequence of the
               human beta T cell receptor locus
           (C) JOURNAL: Science
           (D) VOLUME: 272
           (E) ISSUE: 5269
           (F) PAGES: 1755-1762
```

```
          (G) DATE: 6 21 96
          (H) DOCUMENT NUMBER: MEDLINE 96256474
          (I) FILING DATE:
          (J) PUBLICATION DATE: June 21, 1996
          (K) RELEVANT RESIDUES IN SEQ ID NO: From 130700 to 134500
              (in GenBank sequence)

(xi) SEQUENCE DESCRIPTION: SEQ ID NO: 15:

GGG TAG GAG GCT TCA CAC TT                                          20

(2) INFORMATION FOR SEQ ID NO: 16:

(i) SEQUENCE CHARACTERISTICS:
          (A) LENGTH: 20 BASES
          (B) TYPE: NUCLEIC ACID
          (C) STRANDEDNESS: SINGLE STRANDED
          (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
          (A) ORGANISM: Homo sapiens
          (B) STRAIN: N/A
          (C) INDIVIDUAL ISOLATE: N/A
          (D) DEVELOPMENTAL STAGE: GERM-LINE
          (E) HAPLOTYPE: N/A
          (F) TISSUE TYPE: BLOOD
          (G) CELL TYPE: LEUKOCYTES
          (H) CELL LINE: N/A
          (I) ORGANELLE: NUCLEUS (vii) IMMEDIATE SOURCE:
          (A) LIBRARY: N/A
          (B) CLONE: N/A (viii) POSITION IN GENOME:
          (A) CHROMOSOME/SEGMENT: 7q35
          (B) MAP POSITION: 157 CM FROM THE TOP OF CHROMOSOME 7
          (C) UNITS: centimorgans (ix) FEATURE:
          (A) NAME/KEY: TRYPSINOGEN GENE 1 (TRY4), TRYPSINOGEN GENE 2
              (TRY8)
          (B) LOCATION: GENBANK LOCUS U66061
          (C) IDENTIFICATION METHOD: Comparison of DNA sequences and/or
              restriction enzyme digestion patterns of experimentally
              determined from polymerase chain reaction of genomic DNA
              from patients with hereditary pancreatitis with
              sequence in GenBank locus U66061.
          (D) OTHER INFORMATION: Mutations in trypsinogen are associated
              with a phenotype of recurrent acute pancreatitis,
              chronic pancreatitis and an increased risk for pancreatic
              cancer.

(x) PUBLICATION INFORMATION:
          (A) AUTHORS: Whitcomb DC, Gorry MC, Preston RA, Furey W,
              Sossenheimer MJ, Ulrich CD, Martin SP, Gates Jr LK,
              Amann ST, Toskes, PP, LIDDLE R, MCGRAHT K,
              UOMO G, POST JC, EHRLICH GD
          (B) TITLE: Hereditary pancreatitis is caused by a mutation
              in the cationic trypsinogen gene
          (C) JOURNAL: Nature Genetics
          (D) VOLUME: 14
          (E) ISSUE: 2
          (F) PAGES: 141-5
          (G) DATE:  15-10-96
          (H) DOCUMENT NUMBER: NA
          (I) FILING DATE:
          (J) PUBLICATION DATE: 15-10-96
          (K) RELEVANT RESIDUES IN SEQ ID NO: NA
          (A) AUTHORS: Gorry MC, Gabbaizedeh D, Furey W, Gates Jr LK,
```

```
              Preston RA, Aston CE, Zhang Y, Ulrich C, Ehrlich GD,
              Whitcomb DC
       (B) TITLE: Multiple Mutations in the Cationic Trypsinogen
              Gene are Associated with Hereditary Pancreatitis
       (C) JOURNAL: Gastroenterology
       (D) VOLUME: 113
       (E) ISSUE: 4
       (F) PAGES: 1063-1068
       (G) DATE:  15-10-96
       (H) DOCUMENT NUMBER: NA
       (I) FILING DATE:
       (J) PUBLICATION DATE: OCTOBER 1997
       (K) RELEVANT RESIDUES IN SEQ ID NO: NA
       (A) AUTHORS:Rowen,L, Koop BF, Hood L.
       (B) TITLE: The complete 685-kilobase DNA sequence of the
              human beta T cell receptor locus
       (C) JOURNAL: Science
       (D) VOLUME: 272
       (E) ISSUE: 5269
       (F) PAGES: 1755-1762
       (G) DATE: 6 21 96
       (H) DOCUMENT NUMBER: MEDLINE 96256474
       (I) FILING DATE:
       (J) PUBLICATION DATE: June 21, 1996
       (K) RELEVANT RESIDUES IN SEQ ID NO: From 130700 to 134500
              (in GenBank sequence)

(xi) SEQUENCE DESCRIPTION: SEQ ID NO: 16:

TCT CCA TTT GTC CTG TCT CT                                              20

(2) INFORMATION FOR SEQ ID NO: 17:

(i) SEQUENCE CHARACTERISTICS:
       (A) LENGTH: 21 BASES
       (B) TYPE: NUCLEIC ACID
       (C) STRANDEDNESS: SINGLE STRANDED
       (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
       (A) ORGANISM: Homo sapiens
       (B) STRAIN: N/A
       (C) INDIVIDUAL ISOLATE: N/A
       (D) DEVELOPMENTAL STAGE: GERM-LINE
       (E) HAPLOTYPE: N/A
       (F) TISSUE TYPE: BLOOD
       (G) CELL TYPE: LEUKOCYTES
       (H) CELL LINE: N/A
       (I) ORGANELLE: NUCLEUS (vii) IMMEDIATE SOURCE:
       (A) LIBRARY: N/A
       (B) CLONE: N/A (viii) POSITION IN GENOME:
       (A) CHROMOSOME/SEGMENT: 7q35
       (B) MAP POSITION: 157 CM FROM THE TOP OF CHROMOSOME 7
       (C) UNITS: centimorgans (ix) FEATURE:
       (A) NAME/KEY: TRYPSINOGEN GENE 1 (TRY4), TRYPSINOGEN GENE 2
              (TRY8)
       (B) LOCATION: GENBANK LOCUS U66061
       (C) IDENTIFICATION METHOD: Comparison of DNA sequences and/or
              restriction enzyme digestion patterns of experimentally
              determined from polymerase chain reaction of genomic DNA
              from patients with hereditary pancreatitis with
              sequence in GenBank locus U66061.
       (D) OTHER INFORMATION: Mutations in trypsinogen are associated
              with a phenotype of recurrent acute pancreatitis, chronic
``` pancreatitis and an increased risk for pancreatic cancer.

(x) PUBLICATION INFORMATION:
    (A) AUTHORS: Whitcomb DC, Gorry MC, Preston RA, Furey W,
        Sossenheimer MJ, Ulrich CD, Martin SP, Gates Jr LK,
        Amann ST, Toskes, PP, LIDDLE R, MCGRAHT K,
        UOMO G, POST JC, EHRLICH GD
    (B) TITLE: Hereditary pancreatitis is caused by a mutation
        in the cationic trypsinogen gene
    (C) JOURNAL: Nature Genetics
    (D) VOLUME: 14
    (E) ISSUE: 2
    (F) PAGES: 141-5
    (G) DATE: 15-10-96
    (H) DOCUMENT NUMBER: NA
    (I) FILING DATE:
    (J) PUBLICATION DATE: 15-10-96
    (K) RELEVANT RESIDUES IN SEQ ID NO: NA
    (A) AUTHORS: Gorry MC, Gabbaizedeh D, Furey W, Gates Jr LK,
        Preston RA, Aston CE, Zhang Y, Ulrich C, Ehrlich GD,
        Whitcomb DC
    (B) TITLE: Multiple Mutations in the Cationic Trypsinogen
        Gene are Associated with Hereditary Pancreatitis
    (C) JOURNAL: Gastroenterology
    (D) VOLUME: 113
    (E) ISSUE: 4
    (F) PAGES: 1063-1068
    (G) DATE: 15-10-96
    (H) DOCUMENT NUMBER: NA
    (I) FILING DATE:
    (J) PUBLICATION DATE: OCTOBER 1997
    (K) RELEVANT RESIDUES IN SEQ ID NO: NA
    (A) AUTHORS:Rowen,L, Koop BF, Hood L.
    (B) TITLE: The complete 685-kilobase DNA sequence of the
        human beta T cell receptor locus
    (C) JOURNAL: Science
    (D) VOLUME: 272
    (E) ISSUE: 5269
    (F) PAGES: 1755-1762
    (G) DATE: 6 21 96
    (H) DOCUMENT NUMBER: MEDLINE 96256474
    (I) FILING DATE:
    (J) PUBLICATION DATE: June 21, 1996
    (K) RELEVANT RESIDUES IN SEQ ID NO: From 130700 to 134500
        (in GenBank sequence)

(xi) SEQUENCE DESCRIPTION: SEQ ID NO: 17:

GCA CCA GAG AGA TGC AAA CTA                                           21

(2) INFORMATION FOR SEQ ID NO: 18:

(i) SEQUENCE CHARACTERISTICS:
        (A) LENGTH: 21 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:

```
                (A) LIBRARY: N/A
                (B) CLONE: N/A (viii) POSITION IN GENOME:
                (A) CHROMOSOME/SEGMENT: 7q35
                (B) MAP POSITION: 157 CM FROM THE TOP OF CHROMOSOME 7
                (C) UNITS: centimorgans (ix) FEATURE:
                (A) NAME/KEY: TRYPSINOGEN GENE 1 (TRY4), TRYPSINOGEN GENE 2
                    (TRY8)
                (B) LOCATION: GENBANK LOCUS U66061
                (C) IDENTIFICATION METHOD: Comparison of DNA sequences and/or
                    restriction enzyme digestion patterns of experimentally
                    determined from polymerase chain reaction of genomic DNA
                    from patients with hereditary pancreatitis with
                    sequence in GenBank locus U66061.
                (D) OTHER INFORMATION: Mutations in trypsinogen are associated
                    with a phenotype of recurrent acute pancreatitis, chronic
                    pancreatitis and an increased risk for pancreatic cancer.

(x) PUBLICATION INFORMATION:
                (A) AUTHORS: Whitcomb DC, Gorry MC, Preston RA, Furey W,
                    Sossenheimer MJ, Ulrich CD, Martin SP, Gates Jr LK,
                    Amann ST, Toskes, PP, LIDDLE R, MCGRAHT K,
                    UOMO G, POST JC, EHRLICH GD
                (B) TITLE: Hereditary pancreatitis is caused by a mutation
                    in the cationic trypsinogen gene
                (C) JOURNAL: Nature Genetics
                (D) VOLUME: 14
                (E) ISSUE: 2
                (F) PAGES: 141-5
                (G) DATE:  15-10-96
                (H) DOCUMENT NUMBER: NA
                (I) FILING DATE:
                (J) PUBLICATION DATE: 15-10-96
                (K) RELEVANT RESIDUES IN SEQ ID NO: NA
                (A) AUTHORS: Gorry MC, Gabbaizedeh D, Furey W, Gates Jr LK,
                    Preston RA, Aston CE, Zhang Y, Ulrich C, Ehrlich GD,
                    Whitcomb DC
                (B) TITLE: Multiple Mutations in the Cationic Trypsinogen
                    Gene are Associated with Hereditary Pancreatitis
                (C) JOURNAL: Gastroenterology
                (D) VOLUME: 113
                (E) ISSUE: 4
                (F) PAGES: 1063-1068
                (G) DATE:  15-10-96
                (H) DOCUMENT NUMBER: NA
                (I) FILING DATE:
                (J) PUBLICATION DATE: OCTOBER 1997
                (K) RELEVANT RESIDUES IN SEQ ID NO: NA
                (A) AUTHORS:Rowen,L, Koop BF, Hood L.
                (B) TITLE: The complete 685-kilobase DNA sequence of the
                    human beta T cell receptor locus
                (C) JOURNAL: Science
                (D) VOLUME: 272
                (E) ISSUE: 5269
                (F) PAGES: 1755-1762
                (G) DATE: 6 21 96
                (H) DOCUMENT NUMBER: MEDLINE 96256474
                (I) FILING DATE:
                (J) PUBLICATION DATE: June 21, 1996
                (K) RELEVANT RESIDUES IN SEQ ID NO: From 130700 to 134500
                    (in GenBank sequence)

(xi) SEQUENCE DESCRIPTION: SEQ ID NO: 18:

GGG CTG TGT TCC TCT TCA GTT                                              21

(2) INFORMATION FOR SEQ ID NO: 19:

(i) SEQUENCE CHARACTERISTICS:
              (A) LENGTH: 21 BASES
              (B) TYPE: NUCLEIC ACID
              (C) STRANDEDNESS: SINGLE STRANDED
              (D) TOPOLOGY: LINEAR (ii) MOLECULE TYPE: GENOMIC DNA
```

-continued

```
  (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
            from patients with hereditary pancreatitis with
            sequence in GenBank locus U66061.
        (D) OTHER INFORMATION: Mutations in trypsinogen are associated
            with a phenotype of recurrent acute pancreatitis, chronic
            pancreatitis and an increased risk for pancreatic cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE:  15-10-96
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
        (G) DATE:  15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the
            human beta T cell receptor locus
        (C) JOURNAL: Science
        (D) VOLUME: 272
        (E) ISSUE: 5269
        (F) PAGES: 1755-1762
        (G) DATE: 6 21 96
        (H) DOCUMENT NUMBER: MEDLINE 96256474
```

(I) FILING DATE:
        (J) PUBLICATION DATE: June 21, 1996
        (K) RELEVANT RESIDUES IN SEQ ID NO: From 130700 to 134500
            (in GenBank sequence)

(xi) SEQUENCE DESCRIPTION: SEQ ID NO: 19:

TGG CTC CAT GTC CTT CTC ATG                                          21

(2) INFORMATION FOR SEQ ID NO: 20:

(i) SEQUENCE CHARACTERISTICS:
        (A) LENGTH: 21 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
            from patients with hereditary pancreatitis with
            sequence in GenBank locus U66061.
        (D) OTHER INFORMATION: Mutations in trypsinogen are associated
            with a phenotype of recurrent acute pancreatitis, chronic
            pancreatitis and an increased risk for pancreatic cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE: 15-10-96
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen Gene are Associated with Hereditary Pancreatitis
        (C) JOURNAL: Gastroenterology
        (D) VOLUME: 113
        (E) ISSUE: 4
        (F) PAGES: 1063-1068
        (G) DATE:  15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the
            human beta T cell receptor locus
        (C) JOURNAL: Science
        (D) VOLUME: 272
        (E) ISSUE: 5269
        (F) PAGES: 1755-1762
        (G) DATE: 6 21 96
        (H) DOCUMENT NUMBER: MEDLINE 96256474
        (I) FILING DATE:
        (J) PUBLICATION DATE: June 21, 1996
        (K) RELEVANT RESIDUES IN SEQ ID NO: From 130700 to 134500
            (in GenBank sequence)

(xi) SEQUENCE DESCRIPTION: SEQ ID NO: 20:

ACG CCC ACC ACC TTT TGA GTT                                              21

(2) INFORMATION FOR SEQ ID NO: 21:

(i) SEQUENCE CHARACTERISTICS:
        (A) LENGTH: 21 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
            from patients with hereditary pancreatitis with
            sequence in GenBank locus U66061.
        (D) OTHER INFORMATION: Mutations in trypsinogen are associated
            with a phenotype of recurrent acute pancreatitis,
            chronic pancreatitis and anincreased risk for
            pancreatic cancer.

```
      (x) PUBLICATION INFORMATION:
           (A) AUTHORS: Whitcomb DC, Gorry MC, Preston RA, Furey W,
                Sossenheimer MJ, Ulrich CD, Martin SP, Gates Jr LK,
                Amann ST, Toskes, PP, LIDDLE R, MCGRAHT K,
                UOMO G, POST JC, EHRLICH GD
           (B) TITLE: Hereditary pancreatitis is caused by a mutation
                in the cationic trypsinogen gene
           (C) JOURNAL: Nature Genetics
           (D) VOLUME: 14
           (E) ISSUE: 2
           (F) PAGES: 141-5
           (G) DATE:  15-10-96
           (H) DOCUMENT NUMBER: NA
           (I) FILING DATE:
           (J) PUBLICATION DATE: 15-10-96
           (K) RELEVANT RESIDUES IN SEQ ID NO: NA
           (A) AUTHORS: Gorry MC, Gabbaizedeh D, Furey W, Gates Jr LK,
                Preston RA, Aston CE, Zhang Y, Ulrich C, Ehrlich GD,
                Whitcomb DC
           (B) TITLE: Multiple Mutations in the Cationic Trypsinogen
                Gene are Associated with Hereditary Pancreatitis
           (C) JOURNAL: Gastroenterology
           (D) VOLUME: 113
           (E) ISSUE: 4
           (F) PAGES: 1063-1068
           (G) DATE:  15-10-96
           (H) DOCUMENT NUMBER: NA
           (I) FILING DATE:
           (J) PUBLICATION DATE: OCTOBER 1997
           (K) RELEVANT RESIDUES IN SEQ ID NO: NA
           (A) AUTHORS:Rowen,L, Koop BF, Hood L.
           (B) TITLE: The complete 685-kilobase DNA sequence of the
                human beta T cell receptor locus
           (C) JOURNAL: Science
           (D) VOLUME: 272
           (E) ISSUE: 5269
           (F) PAGES: 1755-1762
           (G) DATE: 6 21 96
           (H) DOCUMENT NUMBER: MEDLINE 96256474
           (I) FILING DATE:
           (J) PUBLICATION DATE: June 21, 1996
           (K) RELEVANT RESIDUES IN SEQ ID NO: From 130700 to
                134500 (in GenBank sequence)

(xi) SEQUENCE DESCRIPTION: SEQ ID NO: 21:

GAG GGA GGC AAG GAT TCA TGT                                          21

(2) INFORMATION FOR SEQ ID NO: 22:

(i) SEQUENCE CHARACTERISTICS:
         (A) LENGTH: 21 BASES
         (B) TYPE: NUCLEIC ACID
         (C) STRANDEDNESS: SINGLE STRANDED
         (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
         (A) ORGANISM: Homo sapiens
         (B) STRAIN: N/A
         (C) INDIVIDUAL ISOLATE: N/A
         (D) DEVELOPMENTAL STAGE: GERM-LINE
         (E) HAPLOTYPE: N/A
         (F) TISSUE TYPE: BLOOD
         (G) CELL TYPE: LEUKOCYTES
         (H) CELL LINE: N/A
         (I) ORGANELLE: NUCLEUS (vii) IMMEDIATE SOURCE:
         (A) LIBRARY: N/A
         (B) CLONE: N/A
```

```
    (viii) POSITION IN GENOME:
          (A) CHROMOSOME/SEGMENT: 7q35
          (B) MAP POSITION: 157 CM FROM THE TOP OF CHROMOSOME 7
          (C) UNITS: centimorgans (ix) FEATURE:
          (A) NAME/KEY: TRYPSINOGEN GENE 1 (TRY4), TRYPSINOGEN GENE 2
              (TRY8)
          (B) LOCATION: GENBANK LOCUS U66061
          (C) IDENTIFICATION METHOD: Comparison of DNA sequences and/or
              restriction enzyme digestion patterns of experimentally
              determined from polymerase chain reaction of genomic DNA
              from patients with hereditary pancreatitis with
              sequence in GenBank locus U66061.
          (D) OTHER INFORMATION: Mutations in trypsinogen are associated
              with a phenotype of recurrent acute pancreatitis, chronic
              pancreatitis and an increased risk for pancreatic cancer.

(x) PUBLICATION INFORMATION:
          (A) AUTHORS: Whitcomb DC, Gorry MC, Preston RA, Furey W,
              Sossenheimer MJ, Ulrich CD, Martin SP, Gates Jr LK,
              Amann ST, Toskes, PP, LIDDLE R, MCGRAHT K,
              UOMO G, POST JC, EHRLICH GD
          (B) TITLE: Hereditary pancreatitis is caused by a mutation
              in the cationic trypsinogen gene
          (C) JOURNAL: Nature Genetics
          (D) VOLUME: 14
          (E) ISSUE: 2
          (F) PAGES: 141-5
          (G) DATE:  15-10-96
          (H) DOCUMENT NUMBER: NA
          (I) FILING DATE:
          (J) PUBLICATION DATE: 15-10-96
          (K) RELEVANT RESIDUES IN SEQ ID NO: NA
          (A) AUTHORS: Gorry MC, Gabbaizedeh D, Furey W, Gates Jr LK,
              Preston RA, Aston CE, Zhang Y, Ulrich C, Ehrlich GD,
              Whitcomb DC
          (B) TITLE: Multiple Mutations in the Cationic Trypsinogen
              Gene are Associated with Hereditary Pancreatitis
          (C) JOURNAL: Gastroenterology
          (D) VOLUME: 113
          (E) ISSUE: 4
          (F) PAGES: 1063-1068
          (G) DATE:  15-10-96
          (H) DOCUMENT NUMBER: NA
          (I) FILING DATE:
          (J) PUBLICATION DATE: OCTOBER 1997
          (K) RELEVANT RESIDUES IN SEQ ID NO: NA
          (A) AUTHORS:Rowen,L, Koop BF, Hood L.
          (B) TITLE: The complete 685-kilobase DNA sequence of the
              human beta T cell receptor locus
          (C) JOURNAL: Science
          (D) VOLUME: 272
          (E) ISSUE: 5269
          (F) PAGES: 1755-1762
          (G) DATE: 6 21 96
          (H) DOCUMENT NUMBER: MEDLINE 96256474
          (I) FILING DATE:
          (J) PUBLICATION DATE: June 21, 1996
          (K) RELEVANT RESIDUES IN SEQ ID NO: From 130700 to 134500
              (in GenBank sequence)

(xi) SEQUENCE DESCRIPTION: SEQ ID NO: 22:

GAA CAG AGA ATG GGC CAC CAT                                              21

(2) INFORMATION FOR SEQ ID NO: 23:

(i) SEQUENCE CHARACTERISTICS:
          (A) LENGTH: 20 BASES
          (B) TYPE: NUCLEIC ACID
          (C) STRANDEDNESS: SINGLE STRANDED
          (D) TOPOLOGY: LINEAR (ii) MOLECULE TYPE: GENOMIC DNA (iii) HYPOTHETICAL: NO
```

```
    (iv) ANTI-SENSE: yes (v) FRAGMENT TYPE: NA (vi) ORIGINAL SOURCE:
         (A) ORGANISM: Homo sapiens
         (B) STRAIN: N/A
         (C) INDIVIDUAL ISOLATE: N/A
         (D) DEVELOPMENTAL STAGE: GERM-LINE
         (E) HAPLOTYPE: N/A
         (F) TISSUE TYPE: BLOOD
         (G) CELL TYPE: LEUKOCYTES
         (H) CELL LINE: N/A
         (I) ORGANELLE: NUCLEUS (vii) IMMEDIATE SOURCE:
         (A) LIBRARY: N/A
         (B) CLONE: N/A (viii) POSITION IN GENOME:
         (A) CHROMOSOME/SEGMENT: 7q35
         (B) MAP POSITION: 157 CM FROM THE TOP OF CHROMOSOME 7
         (C) UNITS: centimorgans (ix) FEATURE:
         (A) NAME/KEY: TRYPSINOGEN GENE 1 (TRY4), TRYPSINOGEN GENE 2
             (TRY8)
         (B) LOCATION: GENBANK LOCUS U66061
         (C) IDENTIFICATION METHOD: Comparison of DNA sequences and/or
             restriction enzyme digestion patterns of experimentally
             determined from polymerase chain reaction of genomic DNA
             from patients with hereditary pancreatitis with
             sequence in GenBank locus U66061.
         (D) OTHER INFORMATION: Mutations in trypsinogen are associated
             with a phenotype of recurrent acute pancreatitis, chronic
             pancreatitis and an increased risk for pancreatic cancer.

(x) PUBLICATION INFORMATION:
         (A) AUTHORS: Whitcomb DC, Gorry MC, Preston RA, Furey W,
             Sossenheimer MJ, Ulrich CD, Martin SP, Gates Jr LK,
             Amann ST, Toskes, PP, LIDDLE R, MCGRAHT K,
             UOMO G, POST JC, EHRLICH GD
         (B) TITLE: Hereditary pancreatitis is caused by a mutation
             in the cationic trypsinogen gene
         (C) JOURNAL: Nature Genetics
         (D) VOLUME: 14
         (E) ISSUE: 2
         (F) PAGES: 141-5
         (G) DATE:  15-10-96
         (H) DOCUMENT NUMBER: NA
         (I) FILING DATE:
         (J) PUBLICATION DATE: 15-10-96
         (K) RELEVANT RESIDUES IN SEQ ID NO: NA
         (A) AUTHORS: Gorry MC, Gabbaizedeh D, Furey W, Gates Jr LK,
             Preston RA, Aston CE, Zhang Y, Ulrich C, Ehrlich GD,
             Whitcomb DC
         (B) TITLE: Multiple Mutations in the Cationic Trypsinogen
             Gene are Associated with Hereditary Pancreatitis
         (C) JOURNAL: Gastroenterology
         (D) VOLUME: 113
         (E) ISSUE: 4
         (F) PAGES: 1063-1068
         (G) DATE:  15-10-96
         (H) DOCUMENT NUMBER: NA
         (I) FILING DATE:
         (J) PUBLICATION DATE: OCTOBER 1997
         (K) RELEVANT RESIDUES IN SEQ ID NO: NA
         (A) AUTHORS:Rowen,L, Koop BF, Hood L.
         (B) TITLE: The complete 685-kilobase DNA sequence of the
             human beta T cell receptor locus
         (C) JOURNAL: Science
         (D) VOLUME: 272
         (E) ISSUE: 5269
         (F) PAGES: 1755-1762
         (G) DATE: 6 21 96
         (H) DOCUMENT NUMBER: MEDLINE 96256474
         (I) FILING DATE:
         (J) PUBLICATION DATE: June 21, 1996
```

```
          (K) RELEVANT RESIDUES IN SEQ ID NO: From 130700 to 134500
              (in GenBank sequence)

(xi) SEQUENCE DESCRIPTION: SEQ ID NO: 23:

CCT TTC TGA AAC AGG TAT CT                                          20

(2) INFORMATION FOR SEQ ID NO: 24:

(i) SEQUENCE CHARACTERISTICS:
          (A) LENGTH: 21 BASES
          (B) TYPE: NUCLEIC ACID
          (C) STRANDEDNESS: SINGLE STRANDED
          (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
          (A) ORGANISM: Homo sapiens
          (B) STRAIN: N/A
          (C) INDIVIDUAL ISOLATE: N/A
          (D) DEVELOPMENTAL STAGE: GERM-LINE
          (E) HAPLOTYPE: N/A
          (F) TISSUE TYPE: BLOOD
          (G) CELL TYPE: LEUKOCYTES
          (H) CELL LINE: N/A
          (I) ORGANELLE: NUCLEUS (vii) IMMEDIATE SOURCE:
          (A) LIBRARY: N/A
          (B) CLONE: N/A (viii) POSITION IN GENOME:
          (A) CHROMOSOME/SEGMENT: 7q35
          (B) MAP POSITION: 157 CM FROM THE TOP OF CHROMOSOME 7
          (C) UNITS: centimorgans (ix) FEATURE:
          (A) NAME/KEY: TRYPSINOGEN GENE 1 (TRY4), TRYPSINOGEN GENE 2
              (TRY8)
          (B) LOCATION: GENBANK LOCUS U66061
          (C) IDENTIFICATION METHOD: Comparison of DNA sequences and/or
              restriction enzyme digestion patterns of experimentally
              determined from polymerase chain reaction of genomic DNA
              from patients with hereditary pancreatitis with
              sequence in GenBank locus U66061.
          (D) OTHER INFORMATION: Mutations in trypsinogen are associated
              with a phenotype of recurrent acute pancreatitis, chronic
              pancreatitis and an increased risk for pancreatic cancer.

(x) PUBLICATION INFORMATION:
          (A) AUTHORS: Whitcomb DC, Gorry MC, Preston RA, Furey W,
              Sossenheimer MJ, Ulrich CD, Martin SP, Gates Jr LK,
              Amann ST, Toskes, PP, LIDDLE R, MCGRAHT K,
              UOMO G, POST JC, EHRLICH GD
          (B) TITLE: Hereditary pancreatitis is caused by a mutation
              in the cationic trypsinogen gene
          (C) JOURNAL: Nature Genetics
          (D) VOLUME: 14
          (E) ISSUE: 2
          (F) PAGES: 141-5
          (G) DATE:  15-10-96
          (H) DOCUMENT NUMBER: NA
          (I) FILING DATE:
          (J) PUBLICATION DATE: 15-10-96
          (K) RELEVANT RESIDUES IN SEQ ID NO: NA
          (A) AUTHORS: Gorry MC, Gabbaizedeh D, Furey W, Gates Jr LK,
              Preston RA, Aston CE, Zhang Y, Ulrich C, Ehrlich GD,
              Whitcomb DC
          (B) TITLE: Multiple Mutations in the Cationic Trypsinogen
              Gene are Associated with Hereditary Pancreatitis
          (C) JOURNAL: Gastroenterology
```

```
          (D) VOLUME: 113
          (E) ISSUE: 4
          (F) PAGES: 1063-1068
          (G) DATE:  15-10-96
          (H) DOCUMENT NUMBER: NA
          (I) FILING DATE:
          (J) PUBLICATION DATE: OCTOBER 1997
          (K) RELEVANT RESIDUES IN SEQ ID NO: NA
          (A) AUTHORS:Rowen,L, Koop BF, Hood L.
          (B) TITLE: The complete 685-kilobase DNA sequence of the
              human beta T cell receptor locus
          (C) JOURNAL: Science
          (D) VOLUME: 272
          (E) ISSUE: 5269
          (F) PAGES: 1755-1762
          (G) DATE: 6 21 96
          (H) DOCUMENT NUMBER: MEDLINE 96256474
          (I) FILING DATE:
          (J) PUBLICATION DATE: June 21, 1996
          (K) RELEVANT RESIDUES IN SEQ ID NO: From 130700 to 134500
              (in GenBank sequence)

(xi) SEQUENCE DESCRIPTION: SEQ ID NO: 24:

TCC AGT GTG AAG GAG TGA GAG                                         21

(2) INFORMATION FOR SEQ ID NO: 25:

(i) SEQUENCE CHARACTERISTICS:
          (A) LENGTH: 21 BASES
          (B) TYPE: NUCLEIC ACID
          (C) STRANDEDNESS: SINGLE STRANDED
          (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
          (A) ORGANISM: Homo sapiens
          (B) STRAIN: N/A
          (C) INDIVIDUAL ISOLATE: N/A
          (D) DEVELOPMENTAL STAGE: GERM-LINE
          (E) HAPLOTYPE: N/A
          (F) TISSUE TYPE: BLOOD
          (G) CELL TYPE: LEUKOCYTES
          (H) CELL LINE: N/A
          (I) ORGANELLE: NUCLEUS (vii) IMMEDIATE SOURCE:
          (A) LIBRARY: N/A
          (B) CLONE: N/A (viii) POSITION IN GENOME:
          (A) CHROMOSOME/SEGMENT: 7q35
          (B) MAP POSITION: 157 CM FROM THE TOP OF CHROMOSOME 7
          (C) UNITS: centimorgans (ix) FEATURE:
          (A) NAME/KEY: TRYPSINOGEN GENE 1 (TRY4), TRYPSINOGEN GENE 2
              (TRY8)
          (B) LOCATION: GENBANK LOCUS U66061
          (C) IDENTIFICATION METHOD: Comparison of DNA sequences and/or
              restriction enzyme digestion patterns of experimentally
              determined from polymerase chain reaction of genomic DNA
              from patients with hereditary pancreatitis with
              sequence in GenBank locus U66061.
          (D) OTHER INFORMATION: Mutations in trypsinogen are associated
              with a phenotype of recurrent acute pancreatitis, chronic
              pancreatitis and an increased risk for pancreatic cancer.

(x) PUBLICATION INFORMATION:
          (A) AUTHORS: Whitcomb DC, Gorry MC, Preston RA, Furey W,
              Sossenheimer MJ, Ulrich CD, Martin SP, Gates Jr LK,
```

```
            Amann ST, Toskes, PP, LIDDLE R, MCGRAHT K,
            UOMO G, POST JC, EHRLICH GD
    (B) TITLE: Hereditary pancreatitis is caused by a mutation
        in the cationic trypsinogen gene
    (C) JOURNAL: Nature Genetics
    (D) VOLUME: 14
    (E) ISSUE: 2
    (F) PAGES: 141-5
    (G) DATE:  15-10-96
    (H) DOCUMENT NUMBER: NA
    (I) FILING DATE:
    (J) PUBLICATION DATE: 15-10-96
    (K) RELEVANT RESIDUES IN SEQ ID NO: NA
    (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
    (B) TITLE: Multiple Mutations in the Cationic Trypsinogen
            Gene are Associated with Hereditary Pancreatitis
    (C) JOURNAL: Gastroenterology
    (D) VOLUME: 113
    (E) ISSUE: 4
    (F) PAGES: 1063-1068
    (G) DATE:  15-10-96
    (H) DOCUMENT NUMBER: NA
    (I) FILING DATE:
    (J) PUBLICATION DATE: OCTOBER 1997
    (K) RELEVANT RESIDUES IN SEQ ID NO: NA
    (A) AUTHORS:Rowen,L, Koop BF, Hood L.
    (B) TITLE: The complete 685-kilobase DNA sequence of the
            human beta T cell receptor locus
    (C) JOURNAL: Science
    (D) VOLUME: 272
    (E) ISSUE: 5269
    (F) PAGES: 1755-1762
    (G) DATE: 6 21 96
    (H) DOCUMENT NUMBER: MEDLINE 96256474
    (I) FILING DATE:
    (J) PUBLICATION DATE: June 21, 1996
    (K) RELEVANT RESIDUES IN SEQ ID NO: From 172600 to 176300
            (in GenBank sequence)

(xi) SEQUENCE DESCRIPTION: SEQ ID NO: 25:

CTT CCC CTG TCT TTC CCA TAT                                          21

(2) INFORMATION FOR SEQ ID NO: 26:

(i) SEQUENCE CHARACTERISTICS:
        (A) LENGTH: 20 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
```

```
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
            from patients with hereditary pancreatitis with
            sequence in GenBank locus U66061.
        (D) OTHER INFORMATION: Mutations in trypsinogen are associated
            with a phenotype of recurrent acute pancreatitis, chronic
            pancreatitis and an increased risk for pancreatic cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE:  15-10-96
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
        (G) DATE:  15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the
            human beta T cell receptor locus
        (C) JOURNAL: Science
        (D) VOLUME: 272
        (E) ISSUE: 5269
        (F) PAGES: 1755-1762
        (G) DATE: 6 21 96
        (H) DOCUMENT NUMBER: MEDLINE 96256474
        (I) FILING DATE:
        (J) PUBLICATION DATE: June 21, 1996
        (K) RELEVANT RESIDUES IN SEQ ID NO: From 172600 to 176300
            (in GenBank sequence)

(xi) SEQUENCE DESCRIPTION: SEQ ID NO: 26:

AGC CTA CTG CTT CAT TTC AT                                          20

(2) INFORMATION FOR SEQ ID NO: 27:

(i) SEQUENCE CHARACTERISTICS:
        (A) LENGTH: 21 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: no
```

```
    (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
            from patients with hereditary pancreatitis with
            sequence in GenBank locus U66061.
        (D) OTHER INFORMATION: Mutations in trypsinogen are associated
            with a phenotype of recurrent acute pancreatitis, chronic
            pancreatitis and an increased risk for pancreatic cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE:  15-10-96
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
        (G) DATE:  15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the
            human beta T cell receptor locus
        (C) JOURNAL: Science
        (D) VOLUME: 272
        (E) ISSUE: 5269
        (F) PAGES: 1755-1762
        (G) DATE: 6 21 96
        (H) DOCUMENT NUMBER: MEDLINE 96256474
        (I) FILING DATE:
        (J) PUBLICATION DATE: June 21, 1996
        (K) RELEVANT RESIDUES IN SEQ ID NO: From 172600 to 176300
            (in GenBank sequence)
```

```
    (xi) SEQUENCE DESCRIPTION: SEQ ID NO: 27:

TGT TTG TGC TGG GAG GAG CAG                                            21

(2) INFORMATION FOR SEQ ID NO: 28:

(i) SEQUENCE CHARACTERISTICS:
        (A) LENGTH: 21 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
            from patients with hereditary pancreatitis with
            sequence in GenBank locus U66061.
        (D) OTHER INFORMATION: Mutations in trypsinogen are associated
            with a phenotype of recurrent acute pancreatitis, chronic
            pancreatitis and an increased risk for pancreatic cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE:  15-10-96
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
```

```
            (G) DATE: 15-10-96
            (H) DOCUMENT NUMBER: NA
            (I) FILING DATE:
            (J) PUBLICATION DATE: OCTOBER 1997
            (K) RELEVANT RESIDUES IN SEQ ID NO: NA
            (A) AUTHORS:Rowen,L, Koop BF, Hood L.
            (B) TITLE: The complete 685-kilobase DNA sequence of the
                human beta T cell receptor locus
            (C) JOURNAL: Science
            (D) VOLUME: 272
            (E) ISSUE: 5269
            (F) PAGES: 1755-1762
            (G) DATE: 6 21 96
            (H) DOCUMENT NUMBER: MEDLINE 96256474
            (I) FILING DATE:
            (J) PUBLICATION DATE: June 21, 1996
            (K) RELEVANT RESIDUES IN SEQ ID NO: From 172600 to 176300
                (in GenBank sequence)

(xi) SEQUENCE DESCRIPTION: SEQ ID NO: 28:

CAA GGA GGA TGG GAA GAA GAA                                              21

(2) INFORMATION FOR SEQ ID NO:29:

(i) SEQUENCE CHARACTERISTICS:
            (A) LENGTH: 22 BASES
            (B) TYPE: NUCLEIC ACID
            (C) STRANDEDNESS: SINGLE STRANDED
            (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
            (A) ORGANISM: Homo sapiens
            (B) STRAIN: N/A
            (C) INDIVIDUAL ISOLATE: N/A
            (D) DEVELOPMENTAL STAGE: GERM-LINE
            (E) HAPLOTYPE: N/A
            (F) TISSUE TYPE: BLOOD
            (G) CELL TYPE: LEUKOCYTES
            (H) CELL LINE: N/A
            (I) ORGANELLE: NUCLEUS (vii) IMMEDIATE SOURCE:
            (A) LIBRARY: N/A
            (B) CLONE: N/A (viii) POSITION IN GENOME:
            (A) CHROMOSOME/SEGMENT: 7q35
            (B) MAP POSITION: 157 CM FROM THE TOP OF CHROMOSOME 7
            (C) UNITS: centimorgans (ix) FEATURE:
            (A) NAME/KEY: TRYPSINOGEN GENE 1 (TRY4), TRYPSINOGEN GENE 2
                (TRY8)
            (B) LOCATION: GENBANK LOCUS U66061
            (C) IDENTIFICATION METHOD: Comparison of DNA sequences and/or
                restriction enzyme digestion patterns of experimentally
                determined from polymerase chain reaction of genomic DNA
                from patients with hereditary pancreatitis with
                sequence in GenBank locus U66061.
            (D) OTHER INFORMATION: Mutations in trypsinogen are associated
                with a phenotype of recurrent acute pancreatitis, chronic
                pancreatitis and an increased risk for pancreatic cancer.

(x) PUBLICATION INFORMATION:
            (A) AUTHORS: Whitcomb DC, Gorry MC, Preston RA, Furey W,
                Sossenheimer MJ, Ulrich CD, Martin SP, Gates Jr LK,
                Amann ST, Toskes, PP, LIDDLE R, MCGRAHT K,
                UOMO G, POST JC, EHRLICH GD
            (B) TITLE: Hereditary pancreatitis is caused by a mutation
```

```
                    in the cationic trypsinogen gene
            (C) JOURNAL: Nature Genetics
            (D) VOLUME: 14
            (E) ISSUE: 2
            (F) PAGES: 141-5
            (G) DATE:   15-10-96
            (H) DOCUMENT NUMBER: NA
            (I) FILING DATE:
            (J) PUBLICATION DATE: 15-10-96
            (K) RELEVANT RESIDUES IN SEQ ID NO: NA
            (A) AUTHORS: Gorry MC, Gabbaizedeh D, Furey W, Gates Jr LK,
                    Preston RA, Aston CE, Zhang Y, Ulrich C, Ehrlich GD,
                    Whitcomb DC
            (B) TITLE: Multiple Mutations in the Cationic Trypsinogen
                    Gene are Associated with Hereditary Pancreatitis
            (C) JOURNAL: Gastroenterology
            (D) VOLUME: 113
            (E) ISSUE: 4
            (F) PAGES: 1063-1068
            (G) DATE:   15-10-96
            (H) DOCUMENT NUMBER: NA
            (I) FILING DATE:
            (J) PUBLICATION DATE: OCTOBER 1997
            (K) RELEVANT RESIDUES IN SEQ ID NO: NA
            (A) AUTHORS:Rowen,L, Koop BF, Hood L.
            (B) TITLE: The complete 685-kilobase DNA sequence of the
                    human beta T cell receptor locus
            (C) JOURNAL: Science
            (D) VOLUME: 272
            (E) ISSUE: 5269
            (F) PAGES: 1755-1762
            (G) DATE: 6 21 96
            (H) DOCUMENT NUMBER: MEDLINE 96256474
            (I) FILING DATE:
            (J) PUBLICATION DATE: June 21, 1996
            (K) RELEVANT RESIDUES IN SEQ ID NO: From 172600 to 176300
                    (in GenBank sequence)

(xi) SEQUENCE DESCRIPTION: SEQ ID NO: 29:

AAG ACT TCA GTG CTT GAG ACA G                                           22

(2) INFORMATION FOR SEQ ID NO: 30:

(i) SEQUENCE CHARACTERISTICS:
        (A) LENGTH: 22 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans
```

-continued

```
    (ix) FEATURE:
         (A) NAME/KEY: TRYPSINOGEN GENE 1 (TRY4), TRYPSINOGEN GENE 2
             (TRY8)
         (B) LOCATION: GENBANK LOCUS U66061
         (C) IDENTIFICATION METHOD: Comparison of DNA sequences and/or
             restriction enzyme digestion patterns of experimentally
             determined from polymerase chain reaction of genomic DNA
             from patients with hereditary pancreatitis with
             sequence in GenBank locus U66061.
         (D) OTHER INFORMATION: Mutations in trypsinogen are associated
             with a phenotype of recurrent acute pancreatitis, chronic
             pancreatitis and an increased risk for pancreatic cancer.

(x) PUBLICATION INFORMATION:
         (A) AUTHORS: Whitcomb DC, Gorry MC, Preston RA, Furey W,
             Sossenheimer MJ, Ulrich CD, Martin SP, Gates Jr LK,
             Amann ST, Toskes, PP, LIDDLE R, MCGRAHT K,
             UOMO G, POST JC, EHRLICH GD
         (B) TITLE: Hereditary pancreatitis is caused by a mutation
             in the cationic trypsinogen gene
         (C) JOURNAL: Nature Genetics
         (D) VOLUME: 14
         (E) ISSUE: 2
         (F) PAGES: 141-5
         (G) DATE:  15-10-96
         (H) DOCUMENT NUMBER: NA
         (I) FILING DATE:
         (J) PUBLICATION DATE: 15-10-96
         (K) RELEVANT RESIDUES IN SEQ ID NO: NA
         (A) AUTHORS: Gorry MC, Gabbaizedeh D, Furey W, Gates Jr LK,
             Preston RA, Aston CE, Zhang Y, Ulrich C, Ehrlich GD,
             Whitcomb DC
         (B) TITLE: Multiple Mutations in the Cationic Trypsinogen
             Gene are Associated with Hereditary Pancreatitis
         (C) JOURNAL: Gastroenterology
         (D) VOLUME: 113
         (E) ISSUE: 4
         (F) PAGES: 1063-1068
         (G) DATE:  15-10-96
         (H) DOCUMENT NUMBER: NA
         (I) FILING DATE:
         (J) PUBLICATION DATE: OCTOBER 1997
         (K) RELEVANT RESIDUES IN SEQ ID NO: NA
         (A) AUTHORS:Rowen,L, Koop BF, Hood L.
         (B) TITLE: The complete 685-kilobase DNA sequence of the
             human beta T cell receptor locus
         (C) JOURNAL: Science
         (D) VOLUME: 272
         (E) ISSUE: 5269
         (F) PAGES: 1755-1762
         (G) DATE: 6 21 96
         (H) DOCUMENT NUMBER: MEDLINE 96256474
         (I) FILING DATE:
         (J) PUBLICATION DATE: June 21, 1996
         (K) RELEVANT RESIDUES IN SEQ ID NO: From 172600 to 176300
             (in GenBank sequence)

(xi) SEQUENCE DESCRIPTION: SEQ ID NO: 30:

TGA GTT ATT TGC CCT GGG ATA G                                           22

(2) INFORMATION FOR SEQ ID NO: 31:

(i) SEQUENCE CHARACTERISTICS:
         (A) LENGTH: 21 BASES
         (B) TYPE: NUCLEIC ACID
         (C) STRANDEDNESS: SINGLE STRANDED
         (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
```

```
          (A) ORGANISM: Homo sapiens
          (B) STRAIN: N/A
          (C) INDIVIDUAL ISOLATE: N/A
          (D) DEVELOPMENTAL STAGE: GERM-LINE
          (E) HAPLOTYPE: N/A
          (F) TISSUE TYPE: BLOOD
          (G) CELL TYPE: LEUKOCYTES
          (H) CELL LINE: N/A
          (I) ORGANELLE: NUCLEUS (vii) IMMEDIATE SOURCE:
          (A) LIBRARY: N/A
          (B) CLONE: N/A (viii) POSITION IN GENOME:
          (A) CHROMOSOME/SEGMENT: 7q35
          (B) MAP POSITION: 157 CM FROM THE TOP OF CHROMOSOME 7
          (C) UNITS: centimorgans (ix) FEATURE:
          (A) NAME/KEY: TRYPSINOGEN GENE 1 (TRY4), TRYPSINOGEN GENE 2
              (TRY8)
          (B) LOCATION: GENBANK LOCUS U66061
          (C) IDENTIFICATION METHOD: Comparison of DNA sequences and/or
              restriction enzyme digestion patterns of experimentally
              determined from polymerase chain reaction of genomic DNA
              from patients with hereditary pancreatitis with
              sequence in GenBank locus U66061.
          (D) OTHER INFORMATION: Mutations in trypsinogen are associated
              with a phenotype of recurrent acute pancreatitis, chronic
              pancreatitis and an increased risk for pancreatic cancer.

(x) PUBLICATION INFORMATION:
          (A) AUTHORS: Whitcomb DC, Gorry MC, Preston RA, Furey W,
              Sossenheimer MJ, Ulrich CD, Martin SP, Gates Jr LK,
              Amann ST, Toskes, PP, LIDDLE R, MCGRAHT K,
              UOMO G, POST JC, EHRLICH GD
          (B) TITLE: Hereditary pancreatitis is caused by a mutation
              in the cationic trypsinogen gene
          (C) JOURNAL: Nature Genetics
          (D) VOLUME: 14
          (E) ISSUE: 2
          (F) PAGES: 141-5
          (G) DATE:  15-10-96
          (H) DOCUMENT NUMBER: NA
          (I) FILING DATE:
          (J) PUBLICATION DATE: 15-10-96
          (K) RELEVANT RESIDUES IN SEQ ID NO: NA
          (A) AUTHORS: Gorry MC, Gabbaizedeh D, Furey W, Gates Jr LK,
              Preston RA, Aston CE, Zhang Y, Ulrich C, Ehrlich GD,
              Whitcomb DC
          (B) TITLE: Multiple Mutations in the Cationic Trypsinogen
              Gene are Associated with Hereditary Pancreatitis
          (C) JOURNAL: Gastroenterology
          (D) VOLUME: 113
          (E) ISSUE: 4
          (F) PAGES: 1063-1068
          (G) DATE:  15-10-96
          (H) DOCUMENT NUMBER: NA
          (I) FILING DATE:
          (J) PUBLICATION DATE: OCTOBER 1997
          (K) RELEVANT RESIDUES IN SEQ ID NO: NA
          (A) AUTHORS:Rowen,L, Koop BF, Hood L.
          (B) TITLE: The complete 685-kilobase DNA sequence of the
              human beta T cell receptor locus
          (C) JOURNAL: Science
          (D) VOLUME: 272
          (E) ISSUE: 5269
          (F) PAGES: 1755-1762
          (G) DATE: 6 21 96
          (H) DOCUMENT NUMBER: MEDLINE 96256474
          (I) FILING DATE:
          (J) PUBLICATION DATE: June 21, 1996
          (K) RELEVANT RESIDUES IN SEQ ID NO: From 172600 to 176300
              (in GenBank sequence)

(xi) SEQUENCE DESCRIPTION: SEQ ID NO: 31:

ATT AGC AGG AAG CAG CCA CAG                                          21
```

-continued (2) INFORMATION FOR SEQ ID NO: 32:

(i) SEQUENCE CHARACTERISTICS:
        (A) LENGTH: 22 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
            from patients with hereditary pancreatitis with
            sequence in GenBank locus U66061.
        (D) OTHER INFORMATION: Mutations in trypsinogen are associated
            with a phenotype of recurrent acute pancreatitis, chronic
            pancreatitis and an increased risk for pancreatic cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE: 15-10-96
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
        (G) DATE: 15-10-96
        (H) DOCUMENT NUMBER: NA
        (I) FILING DATE:

```
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the
            human beta T cell receptor locus
        (C) JOURNAL: Science
        (D) VOLUME: 272
        (E) ISSUE: 5269
        (F) PAGES: 1755-1762
        (G) DATE: 6 21 96
        (H) DOCUMENT NUMBER: MEDLINE 96256474
        (I) FILING DATE:
        (J) PUBLICATION DATE: June 21, 1996
        (K) RELEVANT RESIDUES IN SEQ ID NO: From 172600 to 176300
            (in GenBank sequence)

(xi) SEQUENCE DESCRIPTION: SEQ ID NO: 32:

TCG TCC GTC CTA CCC AAC CTC A                                            22

(2) INFORMATION FOR SEQ ID NO: 33:

(i) SEQUENCE CHARACTERISTICS:
        (A) LENGTH: 20 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
            from patients with hereditary pancreatitis with
            sequence in GenBank locus U66061.
        (D) OTHER INFORMATION: Mutations in trypsinogen are associated
            with a phenotype of recurrent acute pancreatitis, chronic
            pancreatitis and an increased risk for pancreatic cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
```

(E) ISSUE: 2
                (F) PAGES: 141-5
                (G) DATE:  15-10-96
                (H) DOCUMENT NUMBER: NA
                (I) FILING DATE:
                (J) PUBLICATION DATE: 15-10-96
                (K) RELEVANT RESIDUES IN SEQ ID NO: NA
                (A) AUTHORS: Gorry MC, Gabbaizedeh D, Furey W, Gates Jr LK,
                    Preston RA, Aston CE, Zhang Y, Ulrich C, Ehrlich GD,
                    Whitcomb DC
                (B) TITLE: Multiple Mutations in the Cationic Trypsinogen
                    Gene are Associated with Hereditary Pancreatitis
                (C) JOURNAL: Gastroenterology
                (D) VOLUME: 113
                (E) ISSUE: 4
                (F) PAGES: 1063-1068
                (G) DATE:  15-10-96
                (H) DOCUMENT NUMBER: NA
                (I) FILING DATE:
                (J) PUBLICATION DATE: OCTOBER 1997
                (K) RELEVANT RESIDUES IN SEQ ID NO: NA
                (A) AUTHORS:Rowen,L, Koop BF, Hood L.
                (B) TITLE: The complete 685-kilobase DNA sequence of the
                    human beta T cell receptor locus
                (C) JOURNAL: Science
                (D) VOLUME: 272
                (E) ISSUE: 5269
                (F) PAGES: 1755-1762
                (G) DATE: 6 21 96
                (H) DOCUMENT NUMBER: MEDLINE 96256474
                (I) FILING DATE:
                (J) PUBLICATION DATE: June 21, 1996
                (K) RELEVANT RESIDUES IN SEQ ID NO: From 172600 to 176300
                    (in GenBank sequence)

(xi) SEQUENCE DESCRIPTION: SEQ ID NO: 33:

CTT TGA CTC TTC CCC ACT CC                                           20

(2) INFORMATION FOR SEQ ID NO: 34:

(i) SEQUENCE CHARACTERISTICS:
        (A) LENGTH: 21 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)

```
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
            from patients with hereditary pancreatitis with
            sequence in GenBank locus U66061.
        (D) OTHER INFORMATION: Mutations in trypsinogen are associated
            with a phenotype of recurrent acute pancreatitis, chronic
            pancreatitis and an increased risk for pancreatic cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE:  15-10-96
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
        (G) DATE:  15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the
            human beta T cell receptor locus
        (C) JOURNAL: Science
        (D) VOLUME: 272
        (E) ISSUE: 5269
        (F) PAGES: 1755-1762
        (G) DATE: 6 21 96
        (H) DOCUMENT NUMBER: MEDLINE 96256474
        (I) FILING DATE:
        (J) PUBLICATION DATE: June 21, 1996
        (K) RELEVANT RESIDUES IN SEQ ID NO: From 172600 to 176300
            (in GenBank sequence)

(xi) SEQUENCE DESCRIPTION: SEQ ID NO: 34:

AGG GTA GGA GGC TTC ACA CTC                                            21

(2) INFORMATION FOR SEQ ID NO: 35:

(i) SEQUENCE CHARACTERISTICS:
        (A) LENGTH: 20 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
```

```
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
            from patients with hereditary pancreatitis with
            sequence in GenBank locus U66061.
        (D) OTHER INFORMATION: Mutations in trypsinogen are associated
            with a phenotype of recurrent acute pancreatitis, chronic
            pancreatitis and an increased risk for pancreatic cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE:  15-10-96
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
        (G) DATE:  15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the
            human beta T cell receptor locus
        (C) JOURNAL: Science
        (D) VOLUME: 272
        (E) ISSUE: 5269
        (F) PAGES: 1755-1762
        (G) DATE: 6 21 96
        (H) DOCUMENT NUMBER: MEDLINE 96256474
        (I) FILING DATE:
        (J) PUBLICATION DATE: June 21, 1996
        (K) RELEVANT RESIDUES IN SEQ ID NO: From 172600 to 176300
            (in GenBank sequence)

(xi) SEQUENCE DESCRIPTION: SEQ ID NO: 35:

ACC TGC ACT GAC CCA CAT TG     20

(2) INFORMATION FOR SEQ ID NO: 36:
```

(i) SEQUENCE CHARACTERISTICS:
       (A) LENGTH: 21 BASES
       (B) TYPE: NUCLEIC ACID
       (C) STRANDEDNESS: SINGLE STRANDED
       (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
       (A) ORGANISM: Homo sapiens
       (B) STRAIN: N/A
       (C) INDIVIDUAL ISOLATE: N/A
       (D) DEVELOPMENTAL STAGE: GERM-LINE
       (E) HAPLOTYPE: N/A
       (F) TISSUE TYPE: BLOOD
       (G) CELL TYPE: LEUKOCYTES
       (H) CELL LINE: N/A
       (I) ORGANELLE: NUCLEUS (vii) IMMEDIATE SOURCE:
       (A) LIBRARY: N/A
       (B) CLONE: N/A (viii) POSITION IN GENOME:
       (A) CHROMOSOME/SEGMENT: 7q35
       (B) MAP POSITION: 157 CM FROM THE TOP OF CHROMOSOME 7
       (C) UNITS: centimorgans (ix) FEATURE:
       (A) NAME/KEY: TRYPSINOGEN GENE 1 (TRY4), TRYPSINOGEN GENE 2
           (TRY8)
       (B) LOCATION: GENBANK LOCUS U66061
       (C) IDENTIFICATION METHOD: Comparison of DNA sequences and/or
           restriction enzyme digestion patterns of experimentally
           determined from polymerase chain reaction of genomic DNA
           from patients with hereditary pancreatitis with
           sequence in GenBank locus U66061.
       (D) OTHER INFORMATION: Mutations in trypsinogen are associated
           with a phenotype of recurrent acute pancreatitis, chronic
           pancreatitis and an increased risk for pancreatic cancer.

(x) PUBLICATION INFORMATION:
       (A) AUTHORS: Whitcomb DC, Gorry MC, Preston RA, Furey W,
           Sossenheimer MJ, Ulrich CD, Martin SP, Gates Jr LK,
           Amann ST, Toskes, PP, LIDDLE R, MCGRAHT K,
           UOMO G, POST JC, EHRLICH GD
       (B) TITLE: Hereditary pancreatitis is caused by a mutation
           in the cationic trypsinogen gene
       (C) JOURNAL: Nature Genetics
       (D) VOLUME: 14
       (E) ISSUE: 2
       (F) PAGES: 141-5
       (G) DATE: 15-10-96
       (H) DOCUMENT NUMBER: NA
       (I) FILING DATE:
       (J) PUBLICATION DATE: 15-10-96
       (K) RELEVANT RESIDUES IN SEQ ID NO: NA
       (A) AUTHORS: Gorry MC, Gabbaizedeh D, Furey W, Gates Jr LK,
           Preston RA, Aston CE, Zhang Y, Ulrich C, Ehrlich GD,
           Whitcomb DC
       (B) TITLE: Multiple Mutations in the Cationic Trypsinogen
           Gene are Associated with Hereditary Pancreatitis
       (C) JOURNAL: Gastroenterology
       (D) VOLUME: 113
       (E) ISSUE: 4
       (F) PAGES: 1063-1068
       (G) DATE: 15-10-96
       (H) DOCUMENT NUMBER: NA
       (I) FILING DATE:
       (J) PUBLICATION DATE: OCTOBER 1997
       (K) RELEVANT RESIDUES IN SEQ ID NO: NA
       (A) AUTHORS:Rowen,L, Koop BF, Hood L.

```
            (B) TITLE: The complete 685-kilobase DNA sequence of the
                human beta T cell receptor locus
            (C) JOURNAL: Science
            (D) VOLUME: 272
            (E) ISSUE: 5269
            (F) PAGES: 1755-1762
            (G) DATE: 6 21 96
            (H) DOCUMENT NUMBER: MEDLINE 96256474
            (I) FILING DATE:
            (J) PUBLICATION DATE: June 21, 1996
            (K) RELEVANT RESIDUES IN SEQ ID NO: From 172600 to 176300
                (in GenBank sequence)

(xi) SEQUENCE DESCRIPTION: SEQ ID NO: 36:

TTG ATT TTA GGA GCC ACA TCC                                              21

(2) INFORMATION FOR SEQ ID NO: 37:

(i) SEQUENCE CHARACTERISTICS:
            (A) LENGTH: 20 BASES
            (B) TYPE: NUCLEIC ACID
            (C) STRANDEDNESS: SINGLE STRANDED
            (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
            (A) ORGANISM: Homo sapiens
            (B) STRAIN: N/A
            (C) INDIVIDUAL ISOLATE: N/A
            (D) DEVELOPMENTAL STAGE: GERM-LINE
            (E) HAPLOTYPE: N/A
            (F) TISSUE TYPE: BLOOD
            (G) CELL TYPE: LEUKOCYTES
            (H) CELL LINE: N/A
            (I) ORGANELLE: NUCLEUS (vii) IMMEDIATE SOURCE:
            (A) LIBRARY: N/A
            (B) CLONE: N/A (viii) POSITION IN GENOME:
            (A) CHROMOSOME/SEGMENT: 7q35
            (B) MAP POSITION: 157 CM FROM THE TOP OF CHROMOSOME 7
            (C) UNITS: centimorgans (ix) FEATURE:
            (A) NAME/KEY: TRYPSINOGEN GENE 1 (TRY4), TRYPSINOGEN GENE 2
                (TRY8)
            (B) LOCATION: GENBANK LOCUS U66061
            (C) IDENTIFICATION METHOD: Comparison of DNA sequences and/or
                restriction enzyme digestion patterns of experimentally
                determined from polymerase chain reaction of genomic DNA
                from patients with hereditary pancreatitis with sequence
                in GenBank locus U66061.
            (D) OTHER INFORMATION: Mutations in trypsinogen are associated
                with a phenotype of recurrent acute pancreatitis, chronic
                pancreatitis and an increased risk for pancreatic cancer.

(x) PUBLICATION INFORMATION:
            (A) AUTHORS: Whitcomb DC, Gorry MC, Preston RA, Furey W,
                Sossenheimer MJ, Ulrich CD, Martin SP, Gates Jr LK,
                Amann ST, Toskes, PP, LIDDLE R, MCGRAHT K, UOMO G, POST
                JC, EHRLICH GD
            (B) TITLE: Hereditary pancreatitis is caused by a mutation in
                the cationic trypsinogen gene
            (C) JOURNAL: Nature Genetics
            (D) VOLUME: 14
            (E) ISSUE: 2
            (F) PAGES: 141-5
            (G) DATE: 15-10-96
```

```
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
        (G) DATE:  15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the human
            beta T cell receptor locus
        (C) JOURNAL: Science
        (D) VOLUME: 272
        (E) ISSUE: 5269
        (F) PAGES: 1755-1762
        (G) DATE: 6 21 96
        (H) DOCUMENT NUMBER: MEDLINE 96256474
        (I) FILING DATE:
        (J) PUBLICATION DATE: June 21, 1996
        (K) RELEVANT RESIDUES IN SEQ ID NO: From 172600 to 176300
            (in GenBank sequence)

(xi) SEQUENCE DESCRIPTION: SEQ ID NO: 37:

TGC AAA TTC TCA AGG ATG TG                                        20

(2) INFORMATION FOR SEQ ID NO: 38:

(i) SEQUENCE CHARACTERISTICS:
        (A) LENGTH: 21 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction
``` enzyme digestion patterns of experimentally determined
from polymerase chain reaction of genomic DNA from
patients with hereditary pancreatitis with
sequence in GenBank locus U66061.
(D) OTHER INFORMATION: Mutations in trypsinogen are associated
with a phenotype of recurrent acute pancreatitis, chronic
pancreatitis and an increased risk for pancreatic cancer.

(x) PUBLICATION INFORMATION:
(A) AUTHORS: Whitcomb DC, Gorry MC, Preston RA, Furey W,
Sossenheimer MJ, Ulrich CD, Martin SP, Gates Jr LK,
Amann ST, Toskes, PP, LIDDLE R, MCGRAHT K,
UOMO G, POST JC, EHRLICH GD
(B) TITLE: Hereditary pancreatitis is caused by a mutation
in the cationic trypsinogen gene
(C) JOURNAL: Nature Genetics
(D) VOLUME: 14
(E) ISSUE: 2
(F) PAGES: 141-5
(G) DATE: 15-10-96
(H) DOCUMENT NUMBER: NA
(I) FILING DATE:
(J) PUBLICATION DATE: 15-10-96
(K) RELEVANT RESIDUES IN SEQ ID NO: NA
(A) AUTHORS: Gorry MC, Gabbaizedeh D, Furey W, Gates Jr LK,
Preston RA, Aston CE, Zhang Y, Ulrich C, Ehrlich GD,
Whitcomb DC
(B) TITLE: Multiple Mutations in the Cationic Trypsinogen
Gene are Associated with Hereditary Pancreatitis
(C) JOURNAL: Gastroenterology
(D) VOLUME: 113
(E) ISSUE: 4
(F) PAGES: 1063-1068
(G) DATE: 15-10-96
(H) DOCUMENT NUMBER: NA
(I) FILING DATE:
(J) PUBLICATION DATE: OCTOBER 1997
(K) RELEVANT RESIDUES IN SEQ ID NO: NA
(A) AUTHORS:Rowen,L, Koop BF, Hood L.
(B) TITLE: The complete 685-kilobase DNA sequence of the human
beta T cell receptor locus
(C) JOURNAL: Science
(D) VOLUME: 272
(E) ISSUE: 5269
(F) PAGES: 1755-1762
(G) DATE: 6 21 96
(H) DOCUMENT NUMBER: MEDLINE 96256474
(I) FILING DATE:
(J) PUBLICATION DATE: June 21, 1996
(K) RELEVANT RESIDUES IN SEQ ID NO: From 172600 to 176300
(in GenBank sequence)

(xi) SEQUENCE DESCRIPTION: SEQ ID NO: 38:

AGA GAT GGA GGA GGA ATA CAC                                              21

(2) INFORMATION FOR SEQ ID NO: 39:

(i) SEQUENCE CHARACTERISTICS:
(A) LENGTH: 21 BASES
(B) TYPE: NUCLEIC ACID
(C) STRANDEDNESS: SINGLE STRANDED
(D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
(A) ORGANISM: Homo sapiens
(B) STRAIN: N/A
(C) INDIVIDUAL ISOLATE: N/A
(D) DEVELOPMENTAL STAGE: GERM-LINE
(E) HAPLOTYPE: N/A

```
            (F) TISSUE TYPE: BLOOD
            (G) CELL TYPE: LEUKOCYTES
            (H) CELL LINE: N/A
            (I) ORGANELLE: NUCLEUS (vii) IMMEDIATE SOURCE:
            (A) LIBRARY: N/A
            (B) CLONE: N/A (viii) POSITION IN GENOME:
            (A) CHROMOSOME/SEGMENT: 7q35
            (B) MAP POSITION: 157 CM FROM THE TOP OF CHROMOSOME 7
            (C) UNITS: centimorgans (ix) FEATURE:
            (A) NAME/KEY: TRYPSINOGEN GENE 1 (TRY4), TRYPSINOGEN GENE 2
                (TRY8)
            (B) LOCATION: GENBANK LOCUS U66061
            (C) IDENTIFICATION METHOD: Comparison of DNA sequences and/or
                restriction enzyme digestion patterns of experimentally
                determined from polymerase chain reaction of genomic DNA
                from patients with hereditary pancreatitis with
                sequence in GenBank locus U66061.
            (D) OTHER INFORMATION: Mutations in trypsinogen are associated
                with a phenotype of recurrent acute pancreatitis, chronic
                pancreatitis and an increased risk for pancreatic cancer.

(x) PUBLICATION INFORMATION:
            (A) AUTHORS: Whitcomb DC, Gorry MC, Preston RA, Furey W,
                Sossenheimer MJ, Ulrich CD, Martin SP, Gates Jr LK,
                Amann ST, Toskes, PP, LIDDLE R, MCGRAHT K,
                UOMO G, POST JC, EHRLICH GD
            (B) TITLE: Hereditary pancreatitis is caused by a mutation
                in the cationic trypsinogen gene
            (C) JOURNAL: Nature Genetics
            (D) VOLUME: 14
            (E) ISSUE: 2
            (F) PAGES: 141-5
            (G) DATE:  15-10-96
            (H) DOCUMENT NUMBER: NA
            (I) FILING DATE:
            (J) PUBLICATION DATE: 15-10-96
            (K) RELEVANT RESIDUES IN SEQ ID NO: NA
            (A) AUTHORS: Gorry MC, Gabbaizedeh D, Furey W, Gates Jr LK,
                Preston RA, Aston CE, Zhang Y, Ulrich C, Ehrlich GD,
                Whitcomb DC
            (B) TITLE: Multiple Mutations in the Cationic Trypsinogen
                Gene are Associated with Hereditary Pancreatitis
            (C) JOURNAL: Gastroenterology
            (D) VOLUME: 113
            (E) ISSUE: 4
            (F) PAGES: 1063-1068
            (G) DATE:  15-10-96
            (H) DOCUMENT NUMBER: NA
            (I) FILING DATE:
            (J) PUBLICATION DATE: OCTOBER 1997
            (K) RELEVANT RESIDUES IN SEQ ID NO: NA
            (A) AUTHORS:Rowen,L, Koop BF, Hood L.
            (B) TITLE: The complete 685-kilobase DNA sequence of the
                human beta T cell receptor locus
            (C) JOURNAL: Science
            (D) VOLUME: 272
            (E) ISSUE: 5269
            (F) PAGES: 1755-1762
            (G) DATE: 6 21 96
            (H) DOCUMENT NUMBER: MEDLINE 96256474
            (I) FILING DATE:
            (J) PUBLICATION DATE: June 21, 1996
            (K) RELEVANT RESIDUES IN SEQ ID NO: From 172600 to 176300
                (in GenBank sequence)

(xi) SEQUENCE DESCRIPTION: SEQ ID NO: 39:

TGT CTC TTT CTC TGG CCT AAC                                          21

(2) INFORMATION FOR SEQ ID NO: 40:

(i) SEQUENCE CHARACTERISTICS:
```

```
        (A) LENGTH: 21 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
            from patients with hereditary pancreatitis with
            sequence in GenBank locus U66061.
        (D) OTHER INFORMATION: Mutations in trypsinogen are associated
            with a phenotype of recurrent acute pancreatitis,
            chronic pancreatitis and an increased risk for pancreatic
            cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE:  15-10-96
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
        (G) DATE:  15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the
```

```
                    human beta T cell receptor locus
          (C) JOURNAL: Science
          (D) VOLUME: 272
          (E) ISSUE: 5269
          (F) PAGES: 1755-1762
          (G) DATE: 6 21 96
          (H) DOCUMENT NUMBER: MEDLINE 96256474
          (I) FILING DATE:
          (J) PUBLICATION DATE: June 21, 1996
          (K) RELEVANT RESIDUES IN SEQ ID NO: From 172600 to 176300
              (in GenBank sequence)

(xi) SEQUENCE DESCRIPTION: SEQ ID NO: 40:

CAC CTT GGG AGT TCA AAT CAT                                              21

(2) INFORMATION FOR SEQ ID NO: 41:

(i) SEQUENCE CHARACTERISTICS:
          (A) LENGTH: 20 BASES
          (B) TYPE: NUCLEIC ACID
          (C) STRANDEDNESS: SINGLE STRANDED
          (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
          (A) ORGANISM: Homo sapiens
          (B) STRAIN: N/A
          (C) INDIVIDUAL ISOLATE: N/A
          (D) DEVELOPMENTAL STAGE: GERM-LINE
          (E) HAPLOTYPE: N/A
          (F) TISSUE TYPE: BLOOD
          (G) CELL TYPE: LEUKOCYTES
          (H) CELL LINE: N/A
          (I) ORGANELLE: NUCLEUS (vii) IMMEDIATE SOURCE:
          (A) LIBRARY: N/A
          (B) CLONE: N/A (viii) POSITION IN GENOME:
          (A) CHROMOSOME/SEGMENT: 7q35
          (B) MAP POSITION: 157 CM FROM THE TOP OF CHROMOSOME 7
          (C) UNITS: centimorgans (ix) FEATURE:
          (A) NAME/KEY: TRYPSINOGEN GENE 1 (TRY4), TRYPSINOGEN GENE 2
              (TRY8)
          (B) LOCATION: GENBANK LOCUS U66061
          (C) IDENTIFICATION METHOD: Comparison of DNA sequences and/or
              restriction enzyme digestion patterns of experimentally
              determined from polymerase chain reaction of genomic DNA
              from patients with hereditary pancreatitis with
              sequence in GenBank locus U66061.
          (D) OTHER INFORMATION: Mutations in trypsinogen are associated
              with a phenotype of recurrent acute pancreatitis, chronic
              pancreatitis and an increased risk for pancreatic cancer.

(x) PUBLICATION INFORMATION:
          (A) AUTHORS: Whitcomb DC, Gorry MC, Preston RA, Furey W,
              Sossenheimer MJ, Ulrich CD, Martin SP, Gates Jr LK,
              Amann ST, Toskes, PP, LIDDLE R, MCGRAHT K,
              UOMO G, POST JC, EHRLICH GD
          (B) TITLE: Hereditary pancreatitis is caused by a mutation
              in the cationic trypsinogen gene
          (C) JOURNAL: Nature Genetics
          (D) VOLUME: 14
          (E) ISSUE: 2
          (F) PAGES: 141-5
          (G) DATE: 15-10-96
          (H) DOCUMENT NUMBER: NA
```

```
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
        (G) DATE:  15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the
            human beta T cell receptor locus
        (C) JOURNAL: Science
        (D) VOLUME: 272
        (E) ISSUE: 5269
        (F) PAGES: 1755-1762
        (G) DATE: 6 21 96
        (H) DOCUMENT NUMBER: MEDLINE 96256474
        (I) FILING DATE:
        (J) PUBLICATION DATE: June 21, 1996
        (K) RELEVANT RESIDUES IN SEQ ID NO: From 172600 to 176300
            (in GenBank sequence)

(xi) SEQUENCE DESCRIPTION: SEQ ID NO: 41:

GCC CCA CCA GGG AAA ATG AT                                     20

(2) INFORMATION FOR SEQ ID NO: 42:

(i) SEQUENCE CHARACTERISTICS:
        (A) LENGTH: 20 BASES
        (B) TYPE: NUCLEIC ACID
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
```

```
              from patients with hereditary pancreatitis with
              sequence in GenBank locus U66061.
         (D) OTHER INFORMATION: Mutations in trypsinogen are associated
              with a phenotype of recurrent acute pancreatitis, chronic
              pancreatitis and an increased risk for pancreatic cancer.

(x) PUBLICATION INFORMATION:
         (A) AUTHORS: Whitcomb DC, Gorry MC, Preston RA, Furey W,
              Sossenheimer MJ, Ulrich CD, Martin SP, Gates Jr LK,
              Amann ST, Toskes, PP, LIDDLE R, MCGRAHT K,
              UOMO G, POST JC, EHRLICH GD
         (B) TITLE: Hereditary pancreatitis is caused by a mutation
              in the cationic trypsinogen gene
         (C) JOURNAL: Nature Genetics
         (D) VOLUME: 14
         (E) ISSUE: 2
         (F) PAGES: 141-5
         (G) DATE:  15-10-96
         (H) DOCUMENT NUMBER: NA
         (I) FILING DATE:
         (J) PUBLICATION DATE: 15-10-96
         (K) RELEVANT RESIDUES IN SEQ ID NO: NA
         (A) AUTHORS: Gorry MC, Gabbaizedeh D, Furey W, Gates Jr LK,
              Preston RA, Aston CE, Zhang Y, Ulrich C, Ehrlich GD,
              Whitcomb DC
         (B) TITLE: Multiple Mutations in the Cationic Trypsinogen
              Gene are Associated with Hereditary Pancreatitis
         (C) JOURNAL: Gastroenterology
         (D) VOLUME: 113
         (E) ISSUE: 4
         (F) PAGES: 1063-1068
         (G) DATE:  15-10-96
         (H) DOCUMENT NUMBER: NA
         (I) FILING DATE:
         (J) PUBLICATION DATE: OCTOBER 1997
         (K) RELEVANT RESIDUES IN SEQ ID NO: NA
         (A) AUTHORS:Rowen,L, Koop BF, Hood L.
         (B) TITLE: The complete 685-kilobase DNA sequence of the
              human beta T cell receptor locus
         (C) JOURNAL: Science
         (D) VOLUME: 272
         (E) ISSUE: 5269
         (F) PAGES: 1755-1762
         (G) DATE: 6 21 96
         (H) DOCUMENT NUMBER: MEDLINE 96256474
         (I) FILING DATE:
         (J) PUBLICATION DATE: June 21, 1996
         (K) RELEVANT RESIDUES IN SEQ ID NO: From 172600 to 176300
              (in GenBank sequence)

(xi) SEQUENCE DESCRIPTION: SEQ ID NO: 42:

TTC CAC CTC TTT GTA TGT GT                                          20

(2) INFORMATION FOR SEQ ID NO: 43:

(i) SEQUENCE CHARACTERISTICS:
         (A) LENGTH: 20 BASES
         (B) TYPE: NUCLEIC ACID
         (C) STRANDEDNESS: SINGLE STRANDED
         (D) TOPOLOGY: LINEAR (ii) MOLECULE TYPE: GENOMIC DNA (iii) HYPOTHETICAL: NO (iv) ANTI-SENSE: no (v) FRAGMENT TYPE: NA (vi) ORIGINAL SOURCE:
         (A) ORGANISM: Homo sapiens
         (B) STRAIN: N/A
         (C) INDIVIDUAL ISOLATE: N/A
         (D) DEVELOPMENTAL STAGE: GERM-LINE
         (E) HAPLOTYPE: N/A
         (F) TISSUE TYPE: BLOOD
         (G) CELL TYPE: LEUKOCYTES
```

(H) CELL LINE: N/A
                (I) ORGANELLE: NUCLEUS (vii) IMMEDIATE SOURCE:
                (A) LIBRARY: N/A
                (B) CLONE: N/A (viii) POSITION IN GENOME:
                (A) CHROMOSOME/SEGMENT: 7q35
                (B) MAP POSITION: 157 CM FROM THE TOP OF CHROMOSOME 7
                (C) UNITS: centimorgans (ix) FEATURE:
                (A) NAME/KEY: TRYPSINOGEN GENE 1 (TRY4), TRYPSINOGEN GENE 2
                    (TRY8)
                (B) LOCATION: GENBANK LOCUS U66061
                (C) IDENTIFICATION METHOD: Comparison of DNA sequences and/or
                    restriction enzyme digestion patterns of experimentally
                    determined from polymerase chain reaction of genomic DNA
                    from patients with hereditary pancreatitis with
                    sequence in GenBank locus U66061.
                (D) OTHER INFORMATION: Mutations in trypsinogen are associated
                    with a phenotype of recurrent acute pancreatitis, chronic
                    pancreatitis and an increased risk for pancreatic cancer.

(x) PUBLICATION INFORMATION:
                (A) AUTHORS: Whitcomb DC, Gorry MC, Preston RA, Furey W,
                    Sossenheimer MJ, Ulrich CD, Martin SP, Gates Jr LK,
                    Amann ST, Toskes, PP, LIDDLE R, MCGRAHT K,
                    UOMO G, POST JC, EHRLICH GD
                (B) TITLE: Hereditary pancreatitis is caused by a mutation
                    in the cationic trypsinogen gene
                (C) JOURNAL: Nature Genetics
                (D) VOLUME: 14
                (E) ISSUE: 2
                (F) PAGES: 141-5
                (G) DATE:  15-10-96
                (H) DOCUMENT NUMBER: NA
                (I) FILING DATE:
                (J) PUBLICATION DATE: 15-10-96
                (K) RELEVANT RESIDUES IN SEQ ID NO: NA
                (A) AUTHORS: Gorry MC, Gabbaizedeh D, Furey W, Gates Jr LK,
                    Preston RA, Aston CE, Zhang Y, Ulrich C, Ehrlich GD,
                    Whitcomb DC
                (B) TITLE: Multiple Mutations in the Cationic Trypsinogen
                    Gene are Associated with Hereditary Pancreatitis
                (C) JOURNAL: Gastroenterology
                (D) VOLUME: 113
                (E) ISSUE: 4
                (F) PAGES: 1063-1068
                (G) DATE:  15-10-96
                (H) DOCUMENT NUMBER: NA
                (I) FILING DATE:
                (J) PUBLICATION DATE: OCTOBER 1997
                (K) RELEVANT RESIDUES IN SEQ ID NO: NA
                (A) AUTHORS:Rowen,L, Koop BF, Hood L.
                (B) TITLE: The complete 685-kilobase DNA sequence of the
                    human beta T cell receptor locus
                (C) JOURNAL: Science
                (D) VOLUME: 272
                (E) ISSUE: 5269
                (F) PAGES: 1755-1762
                (G) DATE: 6 21 96
                (H) DOCUMENT NUMBER: MEDLINE 96256474
                (I) FILING DATE:
                (J) PUBLICATION DATE: June 21, 1996
                (K) RELEVANT RESIDUES IN SEQ ID NO: From 172600 to 176300
                    (in GenBank sequence)

(xi) SEQUENCE DESCRIPTION: SEQ ID NO: 43:

CAG AGC AAA TGT AGG TGT AT                                                 20

(2) INFORMATION FOR SEQ ID NO: 44:

(i) SEQUENCE CHARACTERISTICS:
                (A) LENGTH: 20 BASES
                (B) TYPE: NUCLEIC ACID

```
        (C) STRANDEDNESS: SINGLE STRANDED
        (D) TOPOLOGY: LINEAR (ii) MOLECULE TYPE: GENOMIC DNA (iii) HYPOTHETICAL: NO (iv) ANTI-SENSE: yes (v) FRAGMENT TYPE: NA (vi) ORIGINAL SOURCE:
        (A) ORGANISM: Homo sapiens
        (B) STRAIN: N/A
        (C) INDIVIDUAL ISOLATE: N/A
        (D) DEVELOPMENTAL STAGE: GERM-LINE
        (E) HAPLOTYPE: N/A
        (F) TISSUE TYPE: BLOOD
        (G) CELL TYPE: LEUKOCYTES
        (H) CELL LINE: N/A
        (I) ORGANELLE: NUCLEUS (vii) IMMEDIATE SOURCE:
        (A) LIBRARY: N/A
        (B) CLONE: N/A (viii) POSITION IN GENOME:
        (A) CHROMOSOME/SEGMENT: 7q35
        (B) MAP POSITION: 157 CM FROM THE TOP OF CHROMOSOME 7
        (C) UNITS: centimorgans (ix) FEATURE:
        (A) NAME/KEY: TRYPSINOGEN GENE 1 (TRY4), TRYPSINOGEN GENE 2
            (TRY8)
        (B) LOCATION: GENBANK LOCUS U66061
        (C) IDENTIFICATION METHOD: Comparison of DNA sequences and/or
            restriction enzyme digestion patterns of experimentally
            determined from polymerase chain reaction of genomic DNA
            from patients with hereditary pancreatitis with
            sequence in GenBank locus U66061.
        (D) OTHER INFORMATION: Mutations in trypsinogen are associated
            with a phenotype of recurrent acute pancreatitis, chronic
            pancreatitis and an increased risk for pancreatic cancer.

(x) PUBLICATION INFORMATION:
        (A) AUTHORS: Whitcomb DC, Gorry MC, Preston RA, Furey W,
            Sossenheimer MJ, Ulrich CD, Martin SP, Gates Jr LK,
            Amann ST, Toskes, PP, LIDDLE R, MCGRAHT K,
            UOMO G, POST JC, EHRLICH GD
        (B) TITLE: Hereditary pancreatitis is caused by a mutation
            in the cationic trypsinogen gene
        (C) JOURNAL: Nature Genetics
        (D) VOLUME: 14
        (E) ISSUE: 2
        (F) PAGES: 141-5
        (G) DATE:  15-10-96
        (H) DOCUMENT NUMBER: NA
        (I) FILING DATE:
        (J) PUBLICATION DATE: 15-10-96
        (K) RELEVANT RESIDUES IN SEQ ID NO: NA
        (A) AUTHORS: Gorry MC, Gabbaizedeh D, Furey W, Gates Jr LK,
            Preston RA, Aston CE, Zhang Y, Ulrich C, Ehrlich GD,
            Whitcomb DC
        (B) TITLE: Multiple Mutations in the Cationic Trypsinogen
            Gene are Associated with Hereditary Pancreatitis
        (C) JOURNAL: Gastroenterology
        (D) VOLUME: 113
        (E) ISSUE: 4
        (F) PAGES: 1063-1068
        (G) DATE:  15-10-96
        (H) DOCUMENT NUMBER: NA
        (I) FILING DATE:
        (J) PUBLICATION DATE: OCTOBER 1997
        (K) RELEVANT RESIDUES IN SEQ ID NO: NA
        (A) AUTHORS:Rowen,L, Koop BF, Hood L.
        (B) TITLE: The complete 685-kilobase DNA sequence of the
            human beta T cell receptor locus
        (C) JOURNAL: Science
        (D) VOLUME: 272
```

-continued

```
    (E) ISSUE: 5269
    (F) PAGES: 1755-1762
    (G) DATE: 6 21 96
    (H) DOCUMENT NUMBER: MEDLINE 96256474
    (I) FILING DATE:
    (J) PUBLICATION DATE: June 21, 1996
    (K) RELEVANT RESIDUES IN SEQ ID NO: From 172600 to 176300
        (in GenBank sequence)

(xi) SEQUENCE DESCRIPTION: SEQ ID NO: 44:

CTG GAG GCT CTG CTT ATG TT                                              20
```